US008319002B2

(12) United States Patent
Daniels et al.

(10) Patent No.: US 8,319,002 B2
(45) Date of Patent: Nov. 27, 2012

(54) NANOSTRUCTURE-ENHANCED PLATELET BINDING AND HEMOSTATIC STRUCTURES

(75) Inventors: R. Hugh Daniels, Mountain View, CA (US); Esther Li, Fremont, CA (US); Erica J. Rogers, Emerald Hills, CA (US)

(73) Assignee: Nanosys, Inc., Palo Alto, CA (US)

( * ) Notice: Subject to any disclaimer, the term of this patent is extended or adjusted under 35 U.S.C. 154(b) by 259 days.

(21) Appl. No.: 12/720,297

(22) Filed: Mar. 9, 2010

(65) Prior Publication Data
US 2011/0064785 A1    Mar. 17, 2011

Related U.S. Application Data

(63) Continuation-in-part of application No. 12/329,431, filed on Dec. 5, 2008.

(60) Provisional application No. 60/992,827, filed on Dec. 6, 2007, provisional application No. 60/992,865, filed on Dec. 6, 2007.

(51) Int. Cl.
*A61F 13/00* (2006.01)
(52) U.S. Cl. .......................................... 602/41; 602/43
(58) Field of Classification Search .............. 602/41–56; 606/219; 427/2.31
See application file for complete search history.

(56) References Cited

U.S. PATENT DOCUMENTS

| | | | |
|---|---|---|---|
| 4,455,377 A | 6/1984 | Finnerty et al. |
| 5,196,396 A | 3/1993 | Lieber |
| 5,252,835 A | 10/1993 | Lieber et al. |
| 5,332,910 A | 7/1994 | Haraguchi et al. |
| 5,505,928 A | 4/1996 | Alivisatos et al. |
| 5,634,946 A | 6/1997 | Slepian |
| 5,690,807 A | 11/1997 | Clark, Jr. et al. |
| 5,751,018 A | 5/1998 | Alivisatos et al. |
| 5,840,435 A | 11/1998 | Lieber et al. |
| 5,897,945 A | 4/1999 | Lieber et al. |
| 5,976,957 A | 11/1999 | Westwater et al. |
| 5,985,112 A | 11/1999 | Fischer |
| 5,985,328 A | 11/1999 | Chu et al. |
| 5,990,479 A | 11/1999 | Weiss et al. |
| 5,997,832 A | 12/1999 | Lieber et al. |
| 6,036,774 A | 3/2000 | Lieber et al. |
| 6,048,616 A | 4/2000 | Gallagher et al. |

(Continued)

FOREIGN PATENT DOCUMENTS

WO    9629629    9/1996

(Continued)

OTHER PUBLICATIONS

Abiraman, S. et al., "Fibrin glue as an osteoinductive protein in a mouse model" Biomat (2002) 23:3023-3031.

(Continued)

*Primary Examiner* — Michael A. Brown
(74) *Attorney, Agent, or Firm* — Andrew L. Filler

(57) ABSTRACT

Methods, systems, and apparatuses for nanomaterial-enhanced platelet binding and hemostatic medical devices are provided. Hemostatic materials and structures are provided that induce platelet binding, including platelet binding and the coagulation of blood at a wound/opening caused by trauma, a surgical procedure, ulceration, or other cause. Example embodiments include platelet binding devices, hemostatic bandages, hemostatic plugs, and hemostatic formulations. The hemostatic materials and structures may incorporate nanostructures and/or further hemostatic elements such as polymers, silicon nanofibers, silicon dioxide nanofibers, and/or glass beads into a highly absorbent, gelling scaffold. The hemostatic materials and structures may be resorbable.

29 Claims, 23 Drawing Sheets

U.S. PATENT DOCUMENTS

| | | |
|---|---|---|
| 6,099,960 A | 8/2000 | Tennent et al. |
| 6,099,965 A | 8/2000 | Tennent et al. |
| 6,106,913 A | 8/2000 | Scardino et al. |
| 6,130,143 A | 10/2000 | Westwater et al. |
| 6,136,156 A | 10/2000 | El-Shall et al. |
| 6,159,742 A | 12/2000 | Lieber et al. |
| 6,190,634 B1 | 2/2001 | Lieber et al. |
| 6,207,229 B1 | 3/2001 | Bawendi et al. |
| 6,225,198 B1 | 5/2001 | Alivisatos et al. |
| 6,265,333 B1 | 7/2001 | Dzenis et al. |
| 6,268,041 B1 | 7/2001 | Goldstein |
| 6,270,347 B1 | 8/2001 | Webster et al. |
| 6,286,226 B1 | 9/2001 | Jin |
| 6,288,390 B1 | 9/2001 | Siuzdak et al. |
| 6,306,736 B1 | 10/2001 | Alivisatos et al. |
| 6,313,015 B1 | 11/2001 | Lee et al. |
| 6,319,321 B1 | 11/2001 | Hiraga et al. |
| 6,322,895 B1 | 11/2001 | Canham |
| 6,359,288 B1 | 3/2002 | Ying et al. |
| 6,361,861 B2 | 3/2002 | Gao et al. |
| 6,362,011 B1 | 3/2002 | Massey et al. |
| 6,383,923 B1 | 5/2002 | Brown et al. |
| 6,399,177 B1 | 6/2002 | Fonash et al. |
| 6,413,489 B1 | 7/2002 | Ying et al. |
| 6,515,009 B1 | 2/2003 | Kunz et al. |
| 6,586,483 B2 | 7/2003 | Kolb et al. |
| 6,656,966 B2 | 12/2003 | Garvey et al. |
| 6,666,214 B2 | 12/2003 | Canham |
| 6,667,099 B1 | 12/2003 | Greiner et al. |
| 6,669,256 B2 | 12/2003 | Nakayama et al. |
| 6,670,179 B1 | 12/2003 | Mattson et al. |
| 6,689,166 B2 | 2/2004 | Laurencin et al. |
| 6,709,622 B2 | 3/2004 | Billiet et al. |
| 6,713,519 B2 | 3/2004 | Wang et al. |
| 6,720,240 B2 | 4/2004 | Gole et al. |
| 6,737,160 B1 | 5/2004 | Full et al. |
| 6,737,447 B1 | 5/2004 | Smith et al. |
| 6,743,408 B2 | 6/2004 | Lieber et al. |
| 6,766,817 B2 | 7/2004 | Da Silva |
| 6,794,196 B2 | 9/2004 | Fonash et al. |
| 6,808,535 B1 | 10/2004 | Jordan |
| 6,811,957 B1 | 11/2004 | Mau et al. |
| 6,831,017 B1 | 12/2004 | Li et al. |
| 6,872,439 B2 | 3/2005 | Fearing et al. |
| 6,882,051 B2 | 4/2005 | Majumdar et al. |
| 6,896,864 B2 | 5/2005 | Clarke |
| 6,958,216 B2 | 10/2005 | Kelley et al. |
| 6,969,690 B2 | 11/2005 | Zhou et al. |
| 7,011,723 B2 | 3/2006 | Full et al. |
| 7,037,332 B2 | 5/2006 | Kutryk et al. |
| 7,056,409 B2 | 6/2006 | Dubrow |
| 7,057,881 B2 | 6/2006 | Chow et al. |
| 7,064,372 B2 | 6/2006 | Duan et al. |
| 7,067,328 B2 | 6/2006 | Dubrow et al. |
| 7,074,294 B2 | 7/2006 | Dubrow |
| 7,129,554 B2 | 10/2006 | Lieber et al. |
| 7,132,161 B2 | 11/2006 | Knowles et al. |
| 7,135,728 B2 | 11/2006 | Duan et al. |
| 7,147,894 B2 | 12/2006 | Zhou et al. |
| 7,163,659 B2 | 1/2007 | Stasiak et al. |
| 7,181,811 B1 | 2/2007 | Tomanek et al. |
| 7,195,780 B2 | 3/2007 | Dennis et al. |
| 7,229,685 B2 | 6/2007 | Full et al. |
| 7,232,460 B2 | 6/2007 | Erlach et al. |
| 7,972,616 B2 | 7/2011 | Dubrow et al. |
| 2001/0051766 A1 | 12/2001 | Gazdzinski |
| 2002/0001977 A1 | 1/2002 | Gole et al. |
| 2002/0037383 A1 | 3/2002 | Spillman et al. |
| 2002/0061662 A1 | 5/2002 | Boggild |
| 2002/0090725 A1 | 7/2002 | Simpson et al. |
| 2002/0092423 A1 | 7/2002 | Gillingham et al. |
| 2002/0130311 A1 | 9/2002 | Lieber et al. |
| 2003/0059742 A1 | 3/2003 | Webster et al. |
| 2003/0065355 A1 | 4/2003 | Weber |
| 2003/0089899 A1 | 5/2003 | Lieber et al. |
| 2003/0093107 A1 | 5/2003 | Parsonage et al. |
| 2003/0124312 A1 | 7/2003 | Autumn |
| 2003/0146529 A1 | 8/2003 | Chen et al. |
| 2003/0189202 A1 | 10/2003 | Li et al. |
| 2003/0195611 A1 | 10/2003 | Greenhalgh et al. |
| 2003/0211129 A1 | 11/2003 | Spillman et al. |
| 2003/0229393 A1 | 12/2003 | Kutryk et al. |
| 2004/0009598 A1 | 1/2004 | Hench et al. |
| 2004/0018371 A1 | 1/2004 | Mao |
| 2004/0023317 A1 | 2/2004 | Motamedi et al. |
| 2004/0026684 A1 | 2/2004 | Empedocles |
| 2004/0052867 A1 | 3/2004 | Canham |
| 2004/0076822 A1 | 4/2004 | Jagota et al. |
| 2004/0079278 A1 | 4/2004 | Kamins |
| 2004/0098023 A1 | 5/2004 | Lee et al. |
| 2004/0115239 A1 | 6/2004 | Shastri et al. |
| 2004/0244677 A1 | 12/2004 | Takami |
| 2004/0258726 A1 | 12/2004 | Stupp et al. |
| 2005/0011431 A1 | 1/2005 | Samuelson et al. |
| 2005/0017171 A1 | 1/2005 | Samuelson et al. |
| 2005/0038498 A1 | 2/2005 | Dubrow et al. |
| 2005/0048127 A1 | 3/2005 | Brown et al. |
| 2005/0048859 A1 | 3/2005 | Canham et al. |
| 2005/0055078 A1 | 3/2005 | Campbell |
| 2005/0096509 A1 | 5/2005 | Olson |
| 2005/0118494 A1 | 6/2005 | Choi |
| 2005/0148984 A1 | 7/2005 | Lindsay et al. |
| 2005/0156504 A1 | 7/2005 | Takai et al. |
| 2005/0181195 A1 | 8/2005 | Dubrow |
| 2005/0187605 A1 | 8/2005 | Greenhalgh et al. |
| 2005/0221072 A1 | 10/2005 | Dubrow et al. |
| 2005/0245637 A1 | 11/2005 | Hossainy et al. |
| 2005/0260355 A1 | 11/2005 | Weber et al. |
| 2006/0005362 A1 | 1/2006 | Arzt et al. |
| 2006/0034935 A1 | 2/2006 | Pronovost et al. |
| 2006/0051340 A1 | 3/2006 | Uchida et al. |
| 2006/0054936 A1 | 3/2006 | Lieber et al. |
| 2006/0159916 A1 | 7/2006 | Dubrow et al. |
| 2006/0204738 A1* | 9/2006 | Dubrow et al. ............ 428/292.1 |
| 2006/0292125 A1 | 12/2006 | Kellar et al. |
| 2007/0031515 A1 | 2/2007 | Stucky et al. |
| 2007/0141130 A1 | 6/2007 | Villanueva et al. |
| 2007/0154510 A1 | 7/2007 | Wilcher et al. |
| 2007/0154564 A1 | 7/2007 | Stucky et al. |
| 2007/0160653 A1 | 7/2007 | Fischer et al. |
| 2007/0190100 A1 | 8/2007 | Shastri et al. |
| 2007/0212388 A1 | 9/2007 | Patravale et al. |
| 2007/0225631 A1* | 9/2007 | Bowlin et al. .................. 602/52 |
| 2007/0282247 A1 | 12/2007 | Desai et al. |
| 2009/0192429 A1* | 7/2009 | Daniels et al. ................. 602/43 |
| 2011/0111012 A1 | 5/2011 | Pepper et al. |

FOREIGN PATENT DOCUMENTS

| | | |
|---|---|---|
| WO | 9918893 | 4/1999 |
| WO | 0044357 | 8/2000 |
| WO | 03097702 | 11/2003 |

OTHER PUBLICATIONS

Autumn, K. et al., "Adhesive force of a single gecko foot-hair" Nature (2000) 405:681-685.

Bjork, M.T. et al. "One-dimensional Steeplechase for Electron Realized" NanoLetts (2002) 2:86-90.

Cao, YW. et al. "Growth and Properties of Semiconductor Core/Shell Nanocrystals with InAs Cores" J. Am. Chem. Soc. (2000) 122:9692-9702.

Chen, I.W. et al., "Sintering dense nanocrystalline ceramics without final-stage grain growth" Nature (2000) 404 (6774):168-171.

Choi, H. et al., "Surface-modified silica colloid for diagnostic imaging" J. Colloid Interface Sci (2003) 258(2):435-437.

Cui, Y. et al. "Doping and electrical transport in silicon wires" J. Phys. Chem. B. (2000) 104:5213-5216.

Cui, Y et al., "Functional nanoscale electronic devices assembled using silicon nanowire building blocks" Science (2001) 291:851-853.

Cui, Y. et al., "Nanowire nanosensors for highly sensitive and selective detection of biological and chemical species" Science (2001) 293:1289-1292.

Cui, Y. et al. "Diameter-controlled synthesis of single-crystal silicon nanowires" Appl. Phys. Letts. (2001) 78 (15):2214-2216.

Dabbousi, B.O. et al. "(CdSe)ZnS core-shell quantum dots: Synthesis and characterization of a size series of highly luminescent nanocrystallites" J. Phys. Chem. B. (1997) 101:9463-9475.
Davis, D. H. et al., "Immobilization of RGD to <111> silicon surfaces for enhanced cell adhesion and proliferation" Biomaterials (2002) 23:4019-4027.
Duan, X. et al. "General synthesis of compound semiconductor nanowires" Adv. Mater. (2000) 12:298-302.
Duan, X. et al., "Single-nanowire electrically driven lasers" Nature (2003) 421:241-245.
Elias, K.L. et al., "Enhanced functions of osteoblasts on nanometer diameter carbon fibers" Biomaterials (2002) 23:3279-3287.
Flahaut, E. et al. "Carbon nanotube-metal-oxide nanocomposites: microstructure, electrical conductivity and mechanical properties" Acta mater (2000) 48:3803-3812.
Geim, A.K. et al., "Microfabricated adhesive mimicking gecko foot-hair" Nature Materials (2003) 2:461-463.
Greene, L.E. et al., "Low-Temperature Wafer-Scale Production of ZnO Nanowire Arrays" Angew. Chem. Int. Ed. (2003) 42:3031-3034.
Gudicksen, M.S. et al. "Diameter-selective synthesis of semiconductor nanowires" J. Am. Chem. Soc. (2000) 122:8801-8802.
Gudicksen, M.S. et al. "Synthetic control of the diameter and length of single crystal semiconductor nanowires" J. Phys. Chem. (2001) 105:4062-4064.
Gudicksen, M.S. et al. "Growth of nanowire superlattice structures of nanoscale photonics and electronics" Nature (2002) 415:617-620.
Hanekamp C. et al., "Randomized comparison of balloon angioplasty versus silicon carbon-coated stent implantation for de novo lesions in small coronary arteries" Am. J. Cardiol. (2004) 93(10):1233-1237.
Haraguchi, K. et al., "Polarization dependence of light emitted from GaAs p-n junctions in quantum wire crystals" J. Appl. Phys. (1994) 75(8):4220-4225.
Haraguchi, K. et al., "Self organized fabrication of planar GaAs nanowhisker arrays" Appl. Phys. Lett (1996) 69 (3):386-387.
Hiruma, K. et al., "GaAs free-standing auntum-sized wires" J. Appl. Phys. (1993) 74(5):3162-3171.
Huang, Y. et al., "Integrated optoelectronics assembed from semiconductor nanowires" Abstracts of Papers of the ACS (2002) 224:U308.
Jun, Y-W, et al. "Controlled synthesis of multi-armed CdS nanorod architectures using monosurfactant system" J. Am. Chem. Soc. (2001) 123:5150-5151.
Kay, S.et al "Nanostructured polymer/nanophase ceramic composites enhance osteoblast and chondrocyte adhesion" . Tissue Eng. (2002) 8(5):753-761.
Kong, J. et al., "Chemical vapor deposition of methane for single-walled carbon nanotubes," Chem. Phys. Lett (1998) 292:567-574.
Kong, J. et al., "Synthesis of individual single-walled carbon nanotubes on patterned silicon wafers" Nature (1998) 395:878-881.
Liu, C. et al. "Sol-Gel Synthesis of Free-Standing Ferroelectric Lead Zirconate Titanate Nanoparticles" J. Am. Chem. Soc. (2001) 123:4344-4345.
Manna, L. et al. "Synthesis of soluble and processable rod-, arrow-, teardrop-, and tetrapod-shaped CdSe nanocrystals" J. Am. Chem. Soc. (2000) 122:12700-12706.
Manna, L. et al. "Epitaxial growth and photochemical annealing of graded Cds/ZnS shells on colloidal CdSe nanorods" J. Am. Chem. Soc. (2002) 124:7136-7145.
Morales, A.M. et al. "A laser ablation method for the synthesis of crystalling semiconductor nanowires" Science (1998) 279:208-211.
Murayama, Y et al. "Cellular reponses of bioabsorbably polymeric materials and guglielmi detachable coil in experimental aneurysms" Stroke (2002) 33:1120-1128.
Olson, M.E. et al. "Healing of porcine doner sites covered with silver-coated dressings" Eur. J. Surg (2000) 166:486-489.

Peng, X. et al. "Epitaxial growth of highly luminescent CdSe/CdS core/shell nanocrystals with photostability and electronic accessibility" J. Am. Chem. Soc. (1997) 119:7019-7029.
Peng, X. et al. "Shape control of CdSe nanocrystals" Nature (2000) 404:59-61.
Price, R.L. et al., "Nanometer surface roughness increases select osteoblast adhesion on carbon nanofiber compacts" J. Biomed. Mat. Res. (2004) 70A(1):129-138.
Puleo, D.A. et al. "Understanding and controlling the bone-implant interface" Biomaterials (1999) 20:2311-2321.
Puntes, V.F. et al. "Colloidal nanocrystal shape and size control: The case of cobalt" Science (2001) 291:2115-2117.
Ritala, M. et al. "Atomic layer epitaxy—a valuable tool for nanotechnology" Nanotech (1999) 10:19-24.
Schon, J.H. et al., "Self-assembled monolayer organic field effect transistors" Nature (2001) 413:713-716.
Shastri, V.P., "Non-degradable biocompatible polymers in medicine: past, present and future" Curr Pharm. Biotechnol. (2003) 4(5):331-337.
Silva, G.A. et al., "Selective differentiation of neural progenitor cells by high-epitope density nanfibers" Science (2004) 303:1352-1355.
Soppimath, K.S. et al. "Biodegradable polymeric nanoparticles as drug delivery devices" J. Controlled Release (2001) 70:1-20.
Suzuki, R. et al. "Inhibition of inflammatory species by titanium surfaces" Clin Orthopaed (2000) 372:280-289.
Thess, A. et al., "Crystalline ropes of metallic carbon nanotubes" Science (1996) 273:483-487.
Turner, S. et al. "Cell attachment on silicon nanostructures" J. Vac. Sci. Technol. B (1997) 15(6):2848-2854.
Urban, J.J. et al. "Synthesis of single-crystalline perovskite nanowires composed of brium titanate and strontium titanate" J. Am. Chem. Soc. (2002) 124:1186-1187.
Uzan, M. et al. "A new aneurysm wrapping material: polyglactin 910 + fibrin sealant" Neurosurg. Rev. (1996) 19:89-91.
Webster, T.J. et al., "Nano-biotechnology: carbon nanofibres as improved neural and orthopaedic implants" Nanotechnology (2004) 15:48-54.
Webster, T.J. et al., "Increased osteoblast adhesion on nanophase metals: Ti, Ti6A14V, and CoCrMo" Biomaterials (2004) 25:4731-4739.
Westwater, J. et al. "Growth of silicon nanowires via gold/silane vapor-liquid-solid reaction" J. Vac. Sci. Technol. B (1997) 15(3):554-557.
Wu, Y. et al. "Block-by-block growth of single-crystalline Si/SiGe superlattice nanowires" NanoLetts (2002) 2:83-86.
Xu, H. et al., "Room-temperature preparation and characterization of poly(ethylene glycol)-coated silica nanoparticles for biomedical applications" J. Biomed. Mat. Res. (2003) 66A(4):870-879.
Xu, H. et al., "Strong and bioactive composites containing nano-silica-fused whiskers for bone repair" Biomaterials (2004) 25:4615-4626.
Yang, P. et al., "Inorganic semiconductor nanowires" Nanoscience (2002) 1(1):1-39.
Yazawa, M. et al., "Semiconductor nanowhiskers" Adv. Mater. (1993) 5(7/8):577-580.
Yun, W.S. et al "Ferroelectric properties of individual barium titanate nanowires investigated by scanned probe microscopy " NanoLetts (2002) 2(5):447-450.
Zhou, C. et al., "Nanoscale metal/self-assumbed monolayer/metal heterostructures" Appl. Phys. Lett (1997) 71 (5):611-613.
Zhou, X.T. et al., "Silicon nanowires as chemical sensors." Chem. Phys. Lett. (2003) 369:220-224.

* cited by examiner

1200

1300

1500 —

Mix an expandable hemostatic material with a pluarlity of nanostructures

3000

3100

3900

NANOSTRUCTURE-ENHANCED PLATELET BINDING AND HEMOSTATIC STRUCTURES

This application is a continuation-in-part of U.S. patent application Ser. No. 12/329,431, filed on Dec. 5, 2008, which claims the benefit of U.S. Provisional Application No. 60/992,827, filed on Dec. 6, 2007, and U.S. Provisional Application No. 60/992,865, filed on Dec. 6, 2007, the entire contents of which are hereby incorporated by reference.

STATEMENT REGARDING FEDERALLY SPONSORED RESEARCH OR DEVELOPMENT

This invention was made with government support under Contract No. N00014-07-C-0008 awarded by the Office of Naval Research. The government may have certain rights in the invention.

BACKGROUND OF THE INVENTION

1. Field of the Invention

The present invention relates to hemostatic materials incorporating various structures, such as nanostructures. The invention further relates to highly absorbent scaffold materials with hemostatic materials incorporated therein. The present invention further relates to materials incorporating nanostructures for enhanced platelet binding.

2. Background of the Invention

Coagulation is a process by which blood forms solid clots. Coagulation is an important part of hemostasis (the process of halting blood flow). During natural hemostasis, a damaged blood vessel wall is covered by a platelet- and fibrin-containing clot to stop bleeding and begin repair of the damaged vessel. Various materials, referred to as "hemostats" or "hemostatic materials," have been developed to help stop wounds from bleeding excessively and to increase a rate of clotting. Such materials may be used in surgical procedures and/or by first responders to traumatic events, for example.

Some hemostatic materials that have been developed are bandage based, including oxidized resorbable cellulose materials, or cotton gauze sponges used to pack wounds prior to the application of pressure. Such bandage based materials are typically not inherently hemostatic, functioning more as absorbers of blood and leading to a plugging of a wound. Products are available that increase the hemostatic activity of a bandage material by incorporating biological agents of the natural physiological clotting cascade, such as thrombin. Such products suffer from cost and stability issues that limit their use. Thus, a need exists to increase the rate of hemostasis on bandage materials, while eliminating the conventional problems of high cost and instability.

Some bulk hemostatic materials exist that are poured into a wound to clot blood, such as QuikClot®, distributed by Z-Medica Corporation, Wallingford, Conn. Such bulk hemostats have disadvantages. For example, such existing bulk hemostats do not function as quickly as desired, may be difficult to apply, and not all existing bulk hemostats can be absorbed by the human body. Furthermore, existing bulk hemostats have an exothermic reaction with blood. Thus, a need exists for bulk hemostatic materials that overcome at least some of these disadvantages.

Biocompatible polymers have also been used as hemostats. For example, resorbable expandable polymers have been used for wound closure to prevent blood loss after endoscopic surgery where the entry/exit point of the endoscopic device is through a blood vessel. An example such device is the Angioseal™ vascular closure device sold by St. Jude Medical, St. Paul, Minn. Absorbent materials, such as cotton gauze or tampon structures, have also been used for wound closure. In a device using an expandable material, blood and/or other fluids are absorbed by the material, and the material swells to cause a physical barrier. Static blood may be entrapped within pores of the material, and the entrapped blood subsequently clots due to stasis. It would be advantageous if the blood within the expanded material could be made to clot more rapidly. One possibility for increasing a rate of clotting is a biological technique using clotting enzymes. However, such a technique would be expensive. A need exists for expandable and/or absorbent material-based devices that have improved rates of clotting, while keeping down device costs.

Current methods of hemostasis, including most surface-based enhancers of coagulation such as zeolite or kaolin clays, trigger coagulation by two mechanisms: (1) providing a surface for activation of the contact (intrinsic) coagulation cascade, and (2) adsorbing water from the blood, thereby concentrating the components of the coagulation cascade at the provided surface. However, such a method of inducing hemostasis is not typical of the physiologically relevant response whereby an activated surface triggers the intrinsic coagulation pathway and also leads to enhanced platelet binding. Thus, there exists a need to provide hemostatic methods and devices which will trigger the intrinsic coagulation pathway and enhance platelet binding to increase the rate of hemostasis.

Inorganic materials have been used as hemostats in various forms. For example, zeolite clays have been used to induce hemostasis. However, these approaches suffer from certain drawbacks such as poor absorptivity of the scaffold material to which they are applied. Thus, there exists a need for a highly absorbent scaffold for the incorporation of hemostatic materials such as inorganic nanostructures. Further, there is a need for a highly absorbent scaffold that will allow larger volumes of blood to be exposed to hemostatic particles incorporated therein.

SUMMARY OF THE INVENTION

Methods, systems, and apparatuses for nanomaterial-enhanced hemostatic medical devices are provided. Hemostatic materials and structures are provided that induce platelet binding and coagulation of blood at a wound/opening caused by trauma, a surgical procedure, ulcerations, or other cause. The hemostatic materials and structures may incorporate nanostructures and/or further hemostatic elements such as polymers and/or glass beads. The hemostatic materials and structures may be durable or resorbable. Example nanomaterial-enhanced hemostatic medical device embodiments include hemostatic bandages, hemostatic plugs, moist dressings, biological dressings, and hemostatic formulations.

The present invention further encompasses methods, systems, and apparatuses for incorporation of inorganic nanostructures (e.g., silicon or silicon dioxide nanofibers) into a base structure material (e.g., a cellulosic base structure) to enhance platelet adhesion and further promote coagulation and clot strength on the base structure. In certain embodiments, the methods, systems, and apparatuses employ inorganic silicon nanofibers for enhancing platelet binding to bandage surfaces to promote coagulation and induce hemostasis.

In a first aspect of the present invention, a hemostatic structure is provided. The hemostatic structure includes a base structure. The base structure may have a variety of forms, including that of a woven material (e.g., weave of fibers) or nonwoven material. The hemostatic structure further includes nanostructures incorporated with the base structure (e.g., a coating of nanostructures on the base structure, a mixing of nanostructures with the material of the base structure, etc.). The nanostructures are configured to induce platelet binding and efficient hemostasis when the hemostatic structure is contacted with blood. Upon binding to the nanostructure surfaces, platelets become activated and provide a surface that accelerates thrombin-induced cleavage of fibrinogen (thrombin burst), enhancing the overall rate and strength of clot formation.

In an example embodiment, the base structure may be a bandage. The material may be cotton (e.g., gauze) or other non-resorbable material. In an alternative aspect, the material may be a resorbable material such as oxidized regenerated cellulose, collagen, gelatin, or glass microfibers.

In another aspect of the invention, a platelet binding device is provided. Nanostructures are integrated with a base structure assembled to receive platelets and promote platelet binding at the nanostructure surfaces. The platelet binding device can include a hemostatic device, a wound-healing device such as a wound dressing, a specific cell binding device; a cell, tissue, or organ targeting device; a platelet collection device, a platelet filtration device, or other devices. As will be appreciated by those of skill in the relevant art(s), platelet binding devices can be suitably formed for any application where platelet binding is desirable.

In yet another aspect of the present invention, a method for forming a hemostatic structure is provided. Nanostructures are incorporated with a material, such as a woven or non-woven substrate material, to form the hemostatic structure. For instance, the material may be coated with nanostructures to form the hemostatic structure. The coating of nanostructures is configured to induce hemostasis when the hemostatic structure is contacted with blood.

In an example, the coating of nanostructures may be performed as follows: A nanostructure suspension is formed. The substrate is mounted in a frame. The mounted substrate is soaked in the nanostructure suspension. The soaked substrate is dried.

In an alternative example, charge-based attraction may be used to coat the substrate material with the nanostructures. For example, the substrate material may be positively or negatively charged, to attract nanostructures having an opposite charge to the substrate material. In an example aspect, the substrate material may be soaked in a solution containing a positively charged polymer to impart a positive charge to the substrate material. The substrate material may be washed and dried. A solution containing the nanostructures may be applied to the substrate material. The nanostructures are attracted from the solution to the substrate material due to the imparted positive charge to coat the substrate material. The coated substrate material may be incubated and dried.

Further techniques may be used alternatively to soaking and/or charge-based attraction to incorporate nanostructures with a substrate material, including nano-spinning, weaving, and/or further techniques described herein.

In another aspect of the present invention, a hemostat includes an expandable hemostatic material and a plurality of nanostructures combined in a mixture. The mixture is configured to be inserted into a wound to plug the wound. The nanostructures are configured to induce coagulation of blood in the wound.

In another aspect of the present invention, a hemostat includes a plurality of glass beads and a plurality of nanostructures. The glass beads and nanostructures are combined to form a mixture. The mixture is configured to induce hemostasis when the hemostat is contacted with blood.

In still another example aspect, a hemostat includes a substrate formed of a plurality of hemostatic particles. Each hemostatic particle is a core material coated with a shell layer. The shell layer is configured to induce coagulation of blood. A rate of resorption of the core material is greater than a rate of resorption of the shell layer, to increase an overall rate of resorption of the hemostatic particles. The hemostat may further include nanostructures, glass beads, and/or other materials mixed with the hemostatic particles.

In still another aspect, a hemostatic bandage includes a bandage material and a nanopowder formed of nanoparticles having an outer thin oxide layer. A coating of nanowires may optionally be formed on a surface of the bandage material. The nanopowder is dispersed in and/or on the bandage material. The thin oxide layer of the nanoparticles may be a naturally-occurring oxide layer.

In still another aspect, a hemostatic bandage includes a bandage material, a first plurality of nanowires formed to each have a first length, and a second plurality of nanowires formed to each have a second length. The second length is greater than the first length. The first plurality of nanowires is dispersed in a first region of the bandage material, and the second plurality of nanowires is dispersed in a second region of the bandage material.

In still another aspect, a surgical staple is provided. The surgical staple has a body having a base portion, a first leg, and a second leg. The first leg extends at a first angle from a first end of a first surface of the base portion, and the second leg extends at a second angle from a second end of the first surface of the base portion. A layer of nanostructures coats at least a portion of the body.

In still another aspect, a surgical suture is provided. The surgical suture includes a thread and a layer of nanostructures that coats at least a portion of the thread.

In yet another embodiment of the present invention, a hemostatic device includes a highly-absorbent scaffold material which allows large volumes of blood to be exposed to hemostatic particles incorporated in the scaffold structure. In one aspect of the present invention, a hemostatic device includes a scaffold comprising a highly-absorbent material which will swell and create a gel to allow large volumes of blood to be exposed to hemostatic particles incorporated in the scaffold. In one embodiment, the hemostatic particles are nanostructures (e.g., silicon or silicon dioxide nanofibers) which induce platelet binding upon contact with blood and allow for improved coagulation and hemostasis. In certain embodiments, the hemostatic device is a pad or bandage comprising the scaffold material. In preferred embodiments of the invention, the scaffold material comprises forms of carboxymethylcellulose (CMC) or alginic acid (alginates). In preferred embodiments, the hemostatic particles are inorganic particles such as silicon nanofibers or silicon dioxide nanofibers.

Further embodiments, features, and advantages of the invention, as well as the structure and operation of the various embodiments of the invention are described in detail below with reference to accompanying drawings.

BRIEF DESCRIPTION OF THE FIGURES

The invention is described with reference to the accompanying drawings. In the drawings, like reference numbers indicate identical or functionally similar elements. The drawing in which an element first appears is indicated by the left-most digit in the corresponding reference number.

Figure 1A:
FIG. 1A is a diagram of a nanowire.

The present invention will now be described with reference to the accompanying drawings. In the drawings, like reference numbers indicate identical or functionally similar elements. Additionally, the left-most digit(s) of a reference number identifies the drawing in which the reference number first appears.

DETAILED DESCRIPTION OF THE INVENTION

It should be appreciated that the particular implementations shown and described herein are examples of the invention and are not intended to otherwise limit the scope of the present invention in any way. Indeed, for the sake of brevity, conventional manufacturing and nanowire (NW), nanorod, nanotube, and nanoribbon technologies and other functional aspects of the systems (and components of the individual operating components of the systems) may not be described in detail herein. Furthermore, for purposes of brevity, the invention is frequently described herein as pertaining to nanowires/nanofibers.

It should be appreciated that although nanowires/nanofibers are frequently referred to, the techniques described herein are also applicable to other nanostructures, such as nanorods, nanotubes, nanotetrapods, nanoribbons and/or combinations thereof. It should further be appreciated that the manufacturing techniques described herein could be used to create any type of bandage or other nanostructure receiving structure, and other medical device types.

As used herein, an "aspect ratio" is the length of a first axis of a nanostructure divided by the average of the lengths of the second and third axes of the nanostructure, where the second and third axes are the two axes whose lengths are most nearly equal to each other. For example, the aspect ratio for a perfect rod would be the length of its long axis divided by the diameter of a cross-section perpendicular to (normal to) the long axis.

The term "heterostructure" when used with reference to nanostructures refers to nanostructures characterized by at least two different and/or distinguishable material types. Typically, one region of the nanostructure comprises a first material type, while a second region of the nanostructure comprises a second material type. In certain embodiments, the nanostructure comprises a core of a first material and at least one shell of a second (or third etc.) material, where the different material types are distributed radially about the long axis of a nanowire, a long axis of an arm of a branched nanocrystal, or the center of a nanocrystal, for example. A shell need not completely cover the adjacent materials to be considered a shell or for the nanostructure to be considered a heterostructure. For example, a nanocrystal characterized by a core of one material covered with small islands of a second material is a heterostructure. In other embodiments, the different material types are distributed at different locations within the nanostructure. For example, material types can be distributed along the major (long) axis of a nanowire or along a long axis of arm of a branched nanocrystal. Different regions within a heterostructure can comprise entirely different materials, or the different regions can comprise a base material.

As used herein, a "nanostructure" is a structure having at least one region or characteristic dimension with a dimension of less than about 500 nm, e.g., less than about 200 nm, less than about 100 nm, less than about 50 nm, or even less than about 20 nm. Typically, the region or characteristic dimension will be along the smallest axis of the structure. Examples of such structures include nanowires, nanorods, nanotubes, branched nanocrystals, nanotetrapods, tripods, bipods, nanocrystals, nanodots, quantum dots, nanoparticles, branched tetrapods (e.g., inorganic dendrimers), and the like. Nanostructures can be substantially homogeneous in material properties, or in certain embodiments can be heterogeneous (e.g., heterostructures). Nanostructures can be, for example, substantially crystalline, substantially monocrystalline, polycrystalline, amorphous, or a combination thereof. In one aspect, each of the three dimensions of the nanostructure has a dimension of less than about 500 nm, for example, less than about 200 nm, less than about 100 nm, less than about 50 nm, or even less than about 20 nm.

The terms "nanofiber" and "nanowire" are used interchangeably herein. As used herein, the terms "nanofiber" and "nanowire" generally refer to any elongated conductive or semiconductive material (or other material described herein) that includes at least one cross-sectional dimension that is less than 500 nm, and preferably, equal to or less than less than about 100 nm, and has an aspect ratio (length:width) of greater than 10, preferably greater than 50, and more preferably, greater than 100. Exemplary nanofibers/nanowires for use in the practice of the methods and systems of the present invention are on the order of 10's of microns long (e.g., about 10, 20, 30, 40, 50 microns, etc.) and about 30-100 nm in diameter.

The nanowires of this invention can be substantially homogeneous in material properties, or in certain embodiments can be heterogeneous (e.g., nanowire heterostructures). The nanowires can be fabricated from essentially any convenient material or materials, and can be, e.g., substantially crystalline, substantially monocrystalline, polycrystalline, or amorphous. Nanowires can have a variable diameter or can have a substantially uniform diameter, that is, a diameter that shows a variance less than about 20% (e.g., less than about 10%, less than about 5%, or less than about 1%) over the region of greatest variability and over a linear dimension of at least 5 nm (e.g., at least 10 nm, at least 20 nm, or at least 50 nm). Typically the diameter is evaluated away from the ends of the nanowire (e.g., over the central 20%, 40%, 50%, or 80% of the nanowire). A nanowire can be straight or can be e.g., curved or bent, over the entire length of its long axis or a portion thereof.

Examples of such nanowires include semiconductor nanowires as described in Published International Patent Application Nos. WO 02/17362, WO 02/48701, and WO 01/03208, carbon nanotubes, and other elongated conductive or semiconductive structures of like dimensions, which are incorporated herein by reference.

As used herein, the term "nanorod" generally refers to any elongated semiconductive material (or other material described herein) similar to a nanowire, but having an aspect ratio (length:width) less than that of a nanowire.

A wide range of types of materials for nanowires, nanorods, nanotubes and nanoribbons can be used, including semiconductor material selected from, e.g., Si, Ge, Sn, Se, Te, B, C (including diamond), P, B—C, B—P($BP_6$), B—Si, Si—C, Si—Ge, Si—Sn and Ge—Sn, SiC, BN, BP, BAs, AN, AlP, AlAs, AlSb, GaN, GaP, GaAs, GaSb, InN, InP, InAs, InSb, ZnO, ZnS, ZnSe, ZnTe, CdS, CdSe, CdTe, HgS, HgSe, HgTe, BeS, BeSe, BeTe, MgS, MgSe, GeS, GeSe, GeTe, SnS, SnSe, SnTe, PbO, PbS, PbSe, PbTe, CuF, CuCl, CuBr, CuI, AgF, AgCl, AgBr, AgI, $BeSiN_2$, $CaCN_2$, $ZnGeP_2$, $CdSnAs_2$, $ZnSnSb_2$, $CuGeP_3$, $CuSi_2P_3$, (Cu, Ag)(Al, Ga, In, Tl, Fe)(S, Se, Te)$_2$, $Si_3N_4$, $Ge_3N_4$, $Al_2O_3$, (Al, Ga, In)$_2$ (S, Se, Te)$_3$, $Al_2CO$, and an appropriate combination of two or more such semiconductors. Other now known or later developed semiconductor materials can be employed. Other types of materials can be used for nanostructures, including metals such as titanium, zirconium, and tantalum, combinations of metals/alloys such as cobalt-chromium or steel, oxides of these metals, and further material types.

Additionally, the nanowires or nanoribbons can include nanotubes formed of semiconductive organic polymer materials, (e.g., pentacene), or transition metal oxides.

Hence, although the term "nanowire" is referred to throughout the description herein for illustrative purposes, it is intended that the description herein also encompass the use of nanotubes (e.g., nanowire-like structures having a hollow tube formed axially therethrough).

It should be understood that the spatial descriptions (e.g., "above", "below", "up", "down", "top", "bottom," "vertical," "horizontal," etc.) made herein are for purposes of illustration only, and that devices of the present invention can be spatially arranged in any orientation or manner.

Figure 1B:
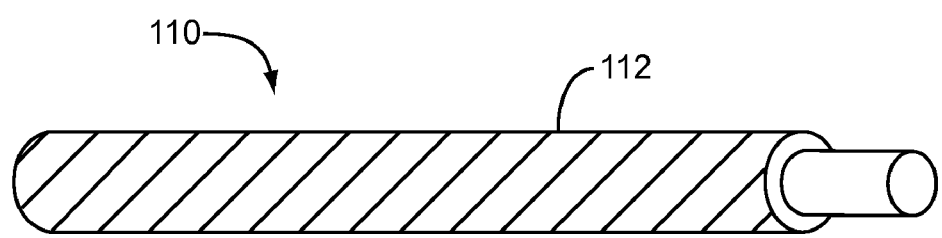
FIG. 1B is a diagram of a nanowire having a core-shell (CS) structure.
Figure 1C:
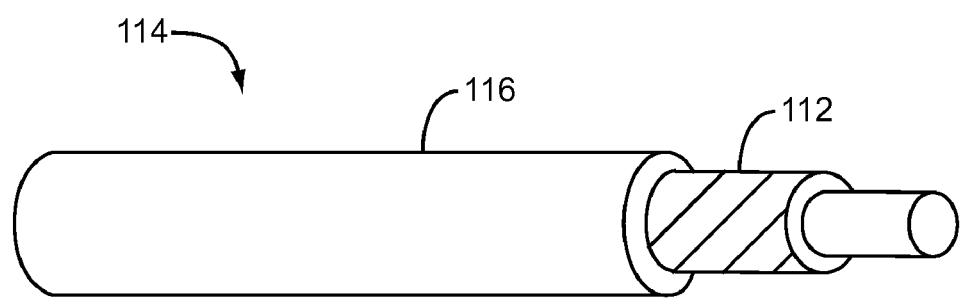
FIG. 1C is a diagram of a nanowire having a core-shell-shell (CSS) structure.

Embodiments of the present invention relate to any type of nanowire. FIG. 1A illustrates a nanowire core (hereafter "nanowire") 100. Nanowire 100 is a single crystal semiconductor or other material, uniform or otherwise. FIG. 1B shows a nanowire 110 having a core-shell structure, with a shell 112 around the nanowire core. An insulating layer, such as an oxide coating, can be formed on a nanowire as the shell layer. Other more complex NW core-shell structures may also be used to include a core of a first material, an inner-shell of a second material, and an outer-shell of a third material, such as shown in FIG. 1C. FIG. 1C shows a nanowire 114 having a core-shell-shell structure, with an inner shell 112 and outer shell 116 around the nanowire core. This can be realized by depositing a layer of TaAlN, WN, or amorphous silicon around the $Si/Si_{O_x}$ core-shell structure (described above) as the outer-gate shell, for example. Note that although a length of the nanowire core (at an end of the nanowire core) is shown exposed (not covered) in FIGS. 1B and 1C, in embodiments, the nanowire core may be completely covered by one or both of shells 112 and 116.

Generally, the core nanostructure can be made from any metallic or semiconductor material, and the one or more shell layers deposited on the core can be made from the same or a different material. For example, the first core material can comprise a first semiconductor selected from the group consisting of: a Group II-VI semiconductor, a Group III-V semiconductor, a Group IV semiconductor, and an alloy thereof. Similarly, the second material of the one or more shell layers can comprise an oxide layer, a second semiconductor, the same as or different from the first semiconductor, e.g., selected from the group consisting of: a Group II-VI semiconductor, a Group III-V semiconductor, a Group IV semiconductor, and an alloy thereof. Example semiconductors include, but are not limited to, CdSe, CdTe, InP, InAs, CdS, ZnS, ZnSe, ZnTe, HgTe, GaN, GaP, GaAs, GaSb, InSb, Si, Ge, AlAs, AlSb, PbSe, PbS, and PbTe.

Nanostructures can be fabricated and their size can be controlled by any of a number of convenient methods that can be adapted to different materials. For example, synthesis of nanocrystals of various composition is described in, e.g., Peng et al. (2000) "Shape Control of CdSe Nanocrystals" Nature 404, 59-61; Puntes et al. (2001) "Colloidal nanocrystal shape and size control: The case of cobalt" Science 291, 2115-2117; U.S. Pat. No. 6,306,736 to Alivisatos et al. (Oct. 23, 2001) entitled "Process for forming shaped group III-V semiconductor nanocrystals, and product formed using process"; U.S. Pat. No. 6,225,198 to Alivisatos et al. (May 1, 2001) entitled "Process for forming shaped group II-VI semiconductor nanocrystals, and product formed using process"; U.S. Pat. No. 5,505,928 to Alivisatos et al. (Apr. 9, 1996) entitled "Preparation of III-V semiconductor nanocrystals"; U.S. Pat. No. 5,751,018 to Alivisatos et al. (May 12, 1998) entitled "Semiconductor nanocrystals covalently bound to solid inorganic surfaces using self-assembled monolayers"; U.S. Pat. No. 6,048,616 to Gallagher et al. (Apr. 11, 2000) entitled "Encapsulated quantum sized doped semiconductor particles and method of manufacturing same"; and U.S. Pat. No. 5,990,479 to Weiss et al. (Nov. 23, 1999) entitled "Organo luminescent semiconductor nanocrystal probes for biological applications and process for making and using such probes."

Growth of nanowires having various aspect ratios, including nanowires with controlled diameters, is described in, e.g., Gudiksen et al (2000) "Diameter-selective synthesis of semiconductor nanowires" J. Am. Chem. Soc. 122, 8801-8802; Cui et al. (2001) "Diameter-controlled synthesis of single-crystal silicon nanowires" Appl. Phys. Lett. 78, 2214-2216; Gudiksen et al. (2001) "Synthetic control of the diameter and length of single crystal semiconductor nanowires" J. Phys. Chem. B 105, 4062-4064; Morales et al. (1998) "A laser ablation method for the synthesis of crystalline semiconductor nanowires" Science 279, 208-211; Duan et al. (2000) "General synthesis of compound semiconductor nanowires" Adv. Mater. 12, 298-302; Cui et al. (2000) "Doping and electrical transport in silicon nanowires" J. Phys. Chem. B 104, 5213-5216; Peng et al. (2000) "Shape control of CdSe nanocrystals" Nature 404, 59-61; Puntes et al. (2001) "Colloidal nanocrystal shape and size control: The case of cobalt" Science 291, 2115-2117; U.S. Pat. No. 6,306,736 to Alivisatos et al. (Oct. 23, 2001) entitled "Process for forming shaped group III-V semiconductor nanocrystals, and product formed using process"; U.S. Pat. No. 6,225,198 to Alivisatos et al. (May 1, 2001) entitled "Process for forming shaped group II-VI semiconductor nanocrystals, and product formed using process"; U.S. Pat. No. 6,036,774 to Lieber et al. (Mar. 14, 2000) entitled "Method of producing metal oxide nanorods"; U.S. Pat. No. 5,897,945 to Lieber et al. (Apr. 27, 1999) entitled "Metal oxide nanorods"; U.S. Pat. No. 5,997,832 to Lieber et al. (Dec. 7, 1999) "Preparation of carbide nanorods"; Urbau et al. (2002) "Synthesis of single-crystalline perovskite nanowires composed of barium titanate and strontium titanate" J. Am. Chem. Soc., 124, 1186; and Yun et al. (2002) "Ferroelectric Properties of Individual Barium Titanate Nanowires Investigated by Scanned Probe Microscopy" Nanoletters 2, 447.

Growth of branched nanowires (e.g., nanotetrapods, tripods, bipods, and branched tetrapods) is described in, e.g., Jun et al. (2001) "Controlled synthesis of multi-armed CdS nanorod architectures using monosurfactant system" J. Am. Chem. Soc. 123, 5150-5151; and Manna et al. (2000) "Synthesis of Soluble and Processable Rod-, Arrow-, Teardrop-, and Tetrapod-Shaped CdSe Nanocrystals" J. Am. Chem. Soc. 122, 12700-12706.

Synthesis of nanoparticles is described in, e.g., U.S. Pat. No. 5,690,807 to Clark Jr. et al. (Nov. 25, 1997) entitled "Method for producing semiconductor particles"; U.S. Pat. No. 6,136,156 to El-Shall, et al. (Oct. 24, 2000) entitled "Nanoparticles of silicon oxide alloys"; U.S. Pat. No. 6,413,489 to Ying et al. (Jul. 2, 2002) entitled "Synthesis of nanometer-sized particles by reverse micelle mediated techniques"; and Liu et al. (2001) "Sol-Gel Synthesis of Free-Standing Ferroelectric Lead Zirconate Titanate Nanoparticles" J. Am. Chem. Soc. 123, 4344. Synthesis of nanoparticles is also described in the above citations for growth of nanocrystals, nanowires, and branched nanowires, where the resulting nanostructures have an aspect ratio less than about 1.5.

Synthesis of core-shell nanostructure heterostructures, namely nanocrystal and nanowire (e.g., nanorod) core-shell heterostructures, are described in, e.g., Peng et al. (1997) "Epitaxial growth of highly luminescent CdSe/CdS core/shell nanocrystals with photostability and electronic accessibility" J. Am. Chem. Soc. 119, 7019-7029; Dabbousi et al. (1997) "(CdSe)ZnS core-shell quantum dots: Synthesis and characterization of a size series of highly luminescent nanocrysallites" J. Phys. Chem. B 101, 9463-9475; Manna et al. (2002) "Epitaxial growth and photochemical annealing of graded CdS/ZnS shells on colloidal CdSe nanorods" J. Am. Chem. Soc. 124, 7136-7145; and Cao et al. (2000) "Growth and properties of semiconductor core/shell nanocrystals with InAs cores" *J. Am. Chem. Soc.* 122, 9692-9702. Similar approaches can be applied to growth of other core-shell nanostructures.

Growth of nanowire heterostructures in which the different materials are distributed at different locations along the long axis of the nanowire is described in, e.g., Gudiksen et al. (2002) "Growth of nanowire superlattice structures for nanoscale photonics and electronics" *Nature* 415, 617-620; Bjork et al. (2002) "One-dimensional steeplechase for electrons realized" *Nano Letters* 2, 86-90; Wu et al. (2002) "Block-by-block growth of single-crystalline Si/SiGe superlattice nanowires" *Nano Letters* 2, 83-86; and U.S. patent application No. 60/370,095 (Apr. 2, 2002) to Empedocles entitled "Nanowire heterostructures for encoding information." Similar approaches can be applied to growth of other heterostructures.

The term "scaffold," as used herein, refers to a support structure to which hemostatic particles can be added to create a hemostatic device. The scaffolds of the present invention can be incorporated into a variety of medical device embodiments including hemostatic bandages, hemostatic plugs, moist dressings, biological dressings, and hemostatic formulations. As will be appreciated by persons of skill in the art, the scaffolds may comprise woven fibers, solid materials, or any other structure known in the art or described herein. The features of the scaffold can be varied to suit the needs of a particular application. For example, the scaffold may be flexible (e.g., a flexible pad for incorporation into a bandage or use as a wound dressing).

Example Hemostatic Material/Structure Embodiments

Embodiments of the present invention relate to medical devices, and in particular relate to materials and structures ("hemostatic materials" and "hemostatic structures") used to reduce/prevent blood loss from trauma, a surgical procedure, ulcerations or other application requiring blood clotting. In embodiments, the materials and structures may incorporate nanostructures and/or further hemostatic materials such as glass beads, core-shell particles, etc. Such nanostructures and/or further hemostatic materials further enhance hemostatic characteristics and/or provide hemostatic properties to the base materials and structures. Example embodiments include hemostatic wound dressings, hemostatic plugs, and other hemostatic formulations such as liquids, powders, foams and gels. The base materials/structures (e.g., a matrix, a substrate, etc.) can be in a bandage format (e.g., gauze, etc.), a gel format that can be squeezed onto a wound (e.g., a bleeding site), a liquid format that can be sprayed or squirted onto a wound, a dry powder that can be sprayed or squirted onto a wound, or a foam that can be extruded/squirted/injected into/onto a wound. A hemostat formed by the combination of base materials/structures and nanostructures (e.g., a nanostructure-enhanced material/structure) may have a solid, liquid, powder, foam, or gel form. A hemostat having a non-solid form may remain in non-solid format upon contact with a wound, may solidify on contact, or may harden shortly after being dispensed, depending on the particular embodiment.

In embodiments, the nanostructure-enhanced materials/structures have a profound effect on inducing hemostasis, reducing blood clotting time as compared to conventional clotting materials, such as QuikClot®, distributed by Z-Medica Corporation, Wallingford, Conn. In some embodiments, the nanostructure-enhanced materials/structures are resorbable (dissolved and assimilated or excreted by a mammalian body). The use of resorbable materials (e.g., silicon nanowires) to induce hemostasis has an advantage of leaving little or no residue after use of the materials. Furthermore, the nanostructure-enhanced materials/structures do not cause a significant increase in temperature during use, as opposed to QuikClot®, which can cause an increase in temperature of about 20 degrees C. or more when used in/on the human body.

Example embodiments are described below, including hemostatic bandage embodiments, expandable hemostatic structures, and hemostatic materials. These example embodiments described herein are provided for illustrative purposes, and are not limiting. Furthermore, additional structural and operational embodiments, including modifications/alterations, will become apparent to persons skilled in the relevant art(s) from the teachings herein. Features of the embodiments described herein may be combined in any manner. Example embodiments of the present invention are described in detail in the following subsections.

Example Hemostatic Bandage Embodiments

In an embodiment, nanostructures, such as inorganic silica nanofibers, are applied onto the surface of bandages/bandage fibers. Such nanostructures (e.g., nanofibers, nanoparticles, etc.) assist in activating the intrinsic (contact) clotting cascade, leading to the slowdown or stoppage of bleeding. The dimensions of the nanostructures are such that they provide an excellent surface for activation of the contact pathway, and thus provide a non-biological way of enhancing clotting on bandage surfaces. Such nanostructures may be nanowires, nanofibers, nanoparticles, and/or any other nanostructure type described herein. Such nanostructures may be made of silicon, silicon having a thin oxide layer, silica, potassium (including potassium nanofibers, nanowires, or nanoparticles), silicon nanostructures functionalized with potassium (e.g., silicon nanofibers functionalized with potassium), etc.

In example embodiments, bandage materials that may be coated and/or otherwise enhanced with nanostructures include resorbable and/or non-resorbable substrate materials such as organic materials, inorganic materials, woven materials/fabrics, nonwoven materials/fabrics (e.g., nonwoven fiber materials such as a cotton ball), synthetic materials (e.g., rayon, nylon/lycra, Gore-Tex®, a film such as a plastic film, etc.), natural materials (e.g., cotton), biologics/biological derived materials (e.g., chitosan, including chitosan microparticles, collagen, gelatin, cellulose, etc.), porous materials, non-porous materials, and/or particles (e.g., glass or polymer beads). For instance, in embodiments, nanofibers may be applied to a resorbable bandage material, such as an oxidized regenerated cellulose (ORC) material (e.g., Surgicel®, which is manufactured by Ethicon, Inc.), a resorbable biopolymer, a gelatin bandage material (e.g., Gelfoam®, which is manufactured by Pfizer Inc.), or a glass microfiber material. The bandage materials may be hemostatic or non-hemostatic. In embodiments, a resorbable, nanostructure-enhanced bandage material may be applied to a wound as a hemostatic bandage/plug to reduce/prevent blood loss, without a subsequent need for removal of the entire bandage material. In another embodiment, nanofibers may be applied to alternate bandage materials that are non-resorbable, to create hemostatic bandage/plugs for the prevention of blood loss. An example of such non-resorbable bandage material is "supergauze" that combines nanofibers with conventional absorbent cotton gauze materials.

Figure 2:
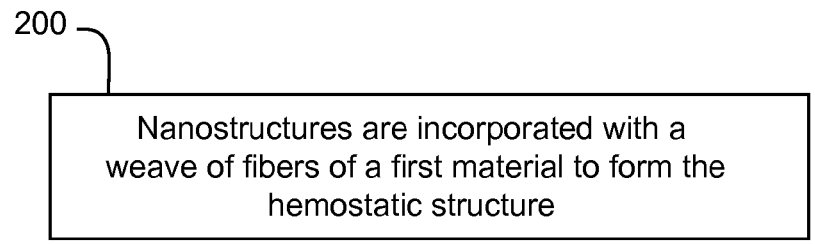
FIG. 2 shows a process for forming a hemostatic structure, according to example embodiments of the present invention.

FIG. 2 shows a step 200 for forming a hemostatic structure, according to example embodiments of the present invention. Step 200 may be used to form hemostatic structures such as hemostatic bandages or plugs. Further structural and operational embodiments will be apparent to persons skilled in the relevant art(s) based on the discussion regarding step 200.

Figure 3:
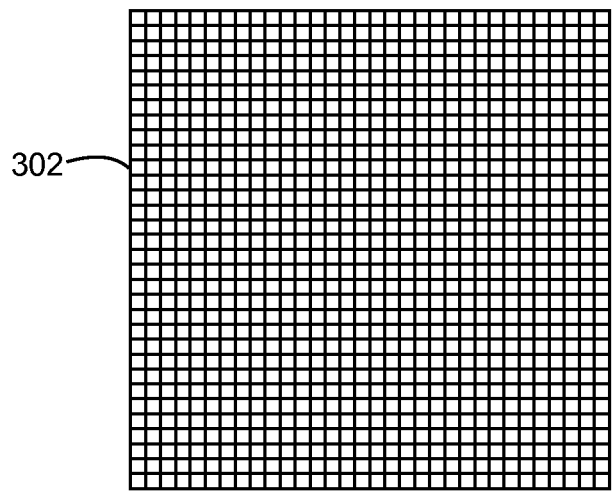
FIG. 3 shows a base structure that is a weave of fibers, according to an example embodiment of the present invention.

As shown in FIG. 2, in step 200, nanostructures are incorporated with a weave of fibers of a first material to form the hemostatic structure. For example, FIG. 3 shows a base structure 300 that is a weave of fibers 302, according to an example embodiment of the present invention. Base structure 300 may be gauze, ORC, a biocompatible polymer such as PGA (polyglycolide), PLA (polylactic acid), PCLA (poly (caprolactone-lactide) random copolymer), or other polymer, a glass microfiber weave, or other type of weave. Fibers 302 may be cotton fibers, cellulose fibers, glass fibers, collagen, or fibers of other material. Note that in an alternative embodiment, base structure 300 may be a solid material, including a plurality of layers of a solid material (e.g., layered ORC) rather than a weave of fibers, may be a nonwoven fiber material such as a cotton ball, or may be another material (woven or nonwoven, hemostatic or non-hemostatic, etc.) mentioned above or elsewhere herein. Nanostructures may be incorporated with (e.g., in and/or on) base structure 300 in any manner, including being coated on base structure 300, being mixed with weave of fibers 302, etc.

As used herein "coating", "coatings", "coated" and "coat" are forms of the same term defining material and process for making a material where a first substance is at least partially covered or associated with a second substance. Both the first and second substance do not have to be different. Further, when a nanostructure is "coated" as used herein, the coating may be may be effectuated by any chemical or mechanical bond or force, including linking agents. Thus a nanowire comprising a first substance may be "coated" with a second substance via a linking agent that is a third substance. As used herein, the "coating" need not be complete or cover the entire surface of the first substance to be "coated." The "coating" may also be complete—i.e., completely covering the first substance. There may be multiple coatings and multiple substances within each coating.

Figure 4:
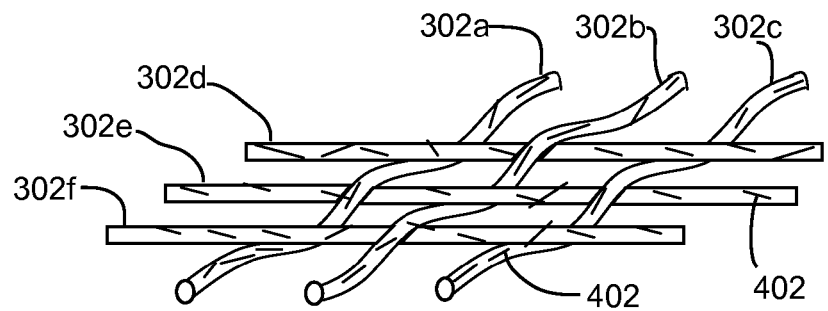
FIG. 4 shows a portion of the base structure shown in FIG. 3 coated with nanostructures according to the process of FIG. 2, according to an embodiment of the present invention.

FIG. 4 shows a magnified view of a portion 400 of base structure 300 of FIG. 3 coated with nanostructures 402 according to step 200 of FIG. 2. As shown in FIG. 4, portion 400 includes fibers 302a-302f. Fibers 302a-302c are woven with fibers 302d-302f. Fibers 302a-302c are aligned along a first axis that is perpendicular to a second axis along which fibers 302d-302f are aligned. Nanostructures 402 coat fibers 302a-302f. Nanostructures 402 are shown as nanofibers in FIG. 4 for illustrative purposes, but in alternative embodiments may include one or more other types of nanostructures described elsewhere herein or otherwise known.

Figure 5:
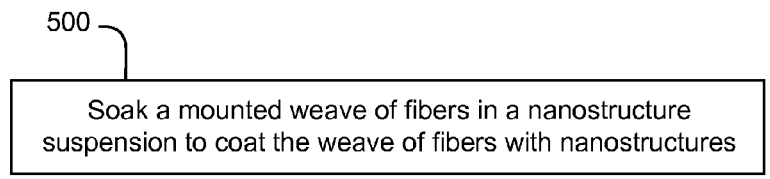
FIGS. 5 and 6 show processes for performing the process of FIG. 2, according to embodiments of the present invention.
Figure 6:
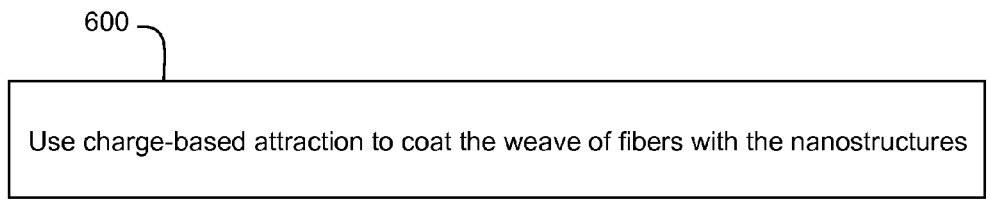

Note that although step 200 recites a weave of fibers, any suitable base structure described herein or otherwise known, woven or un-woven, may have nanostructures incorporated therein. Step 200 of FIG. 2 may be performed in any manner to incorporate nanostructures with a base structure. For example, FIGS. 5 and 6 show example processes for performing step 200, according to embodiments of the present invention. In the embodiment of FIG. 5, in step 500, the weave of fibers may be mounted (e.g., in a frame) and soaked in a nanostructure suspension to coat the weave of fibers with nanostructures. In the embodiment of FIG. 6, in step 600, charge-based attraction is used to coat the weave of fibers with the nanostructures. The embodiments of FIGS. 5 and 6 are described in detail as follows.

Step 500 of FIG. 5 may be performed in any manner. For example, step 500 may be performed according to flowchart 700 of FIG. 7. Flowchart 700 is described as follows. Note that the steps of flowchart 700 do not necessarily need to be performed in the order shown, and that not all of the steps shown in FIG. 7 may need to be performed in all situations. Steps 702-706 illustrate a process of forming a nanostructure suspension. Other techniques for forming a nanostructure suspension may alternatively be used, as would be known to persons skilled in the relevant art(s).

Flowchart 700 begins with step 702. In step 702, a wafer coated with nanostructures is sonicated in a liquid. Any size wafer and suitable liquid may be used. For example, a double sized 4 inch wafer coated with 60 nanometer silicon nanowires may be soaked in ethanol (e.g., soaked in 80 milliliters of ethanol for four minutes).

In step 704, the sonicated nanostructures are filtered. Any suitable filtering technique may be used. For instance, in the current example, the sonicated nanowires may be filtered using a vacuum filter having a 0.45 micrometer filter membrane.

In step 706, the filtered nanostructures are suspended in a liquid to form a nanostructure suspension. Any suitable liquid may be used in step 702. For instance, in the current example, the nanowires may be scraped from the filter membrane, and suspended in ethanol (e.g., 6 milliliters).

Figure 8:
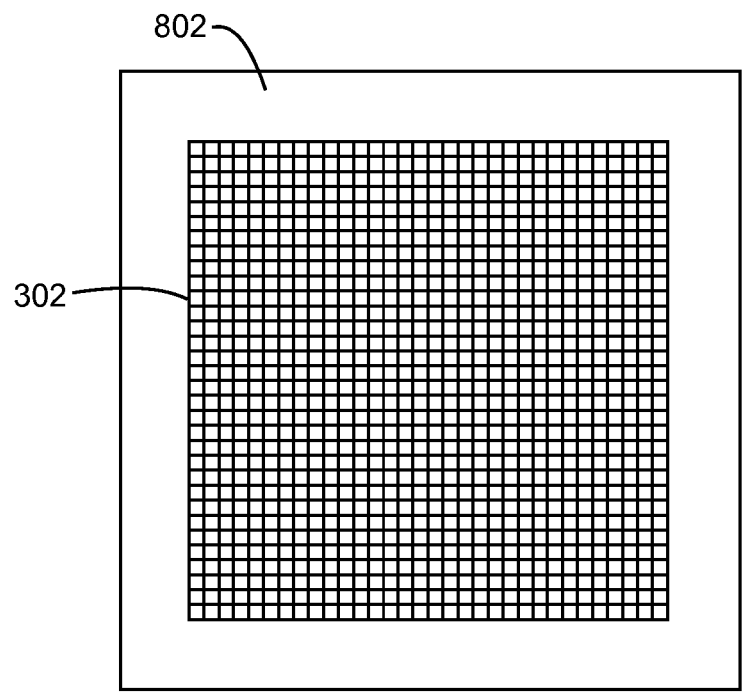
FIG. 8 shows the base structure of FIG. 3 mounted in a frame, according to an example embodiment of the present invention.

In step 708, the weave of fibers is mounted in a frame. For example, FIG. 8 shows base structure 300 of FIG. 3 mounted in a frame 802, according to an example embodiment of the present invention. Base structure 300 may be clamped between first and second portions of frame 802, attached to frame 802 by an adhesive material such as an adhesive tape or epoxy, or may be otherwise mounted to frame 802. Frame 802 may be made from plastic, metal, or other material. In the current example, base structure 300 is gauze. The gauze may be folded as needed to fit frame 802. For example, gauze may be folded into a 2 inch by 2.5 inch rectangle, or other size and/or shape, as needed.

In step 710, the mounted weave of fibers is soaked in the nanostructure suspension. For instance, in the current example, frame 802 and the mounted gauze may be soaked in the nanostructure suspension formed at step 706 for any suitable length of time, such as 4 minutes in the current example. In an embodiment, frame 802 and the mounted gauze may be sonicated while soaking in the nanostructure suspension. The weave of fibers may soak up a portion of all of the nanostructure suspension during step 710, in embodiments.

In step 712, the soaked weave of fibers is dried. The soaked weave of fibers may be dried for any length of time by air drying or by application of heat (e.g., flash drying). For instance, in the current example, frame 802 and the mounted gauze may be placed in an oven (e.g., at 121° C., for 15 minutes) to dry.

Figure 7:
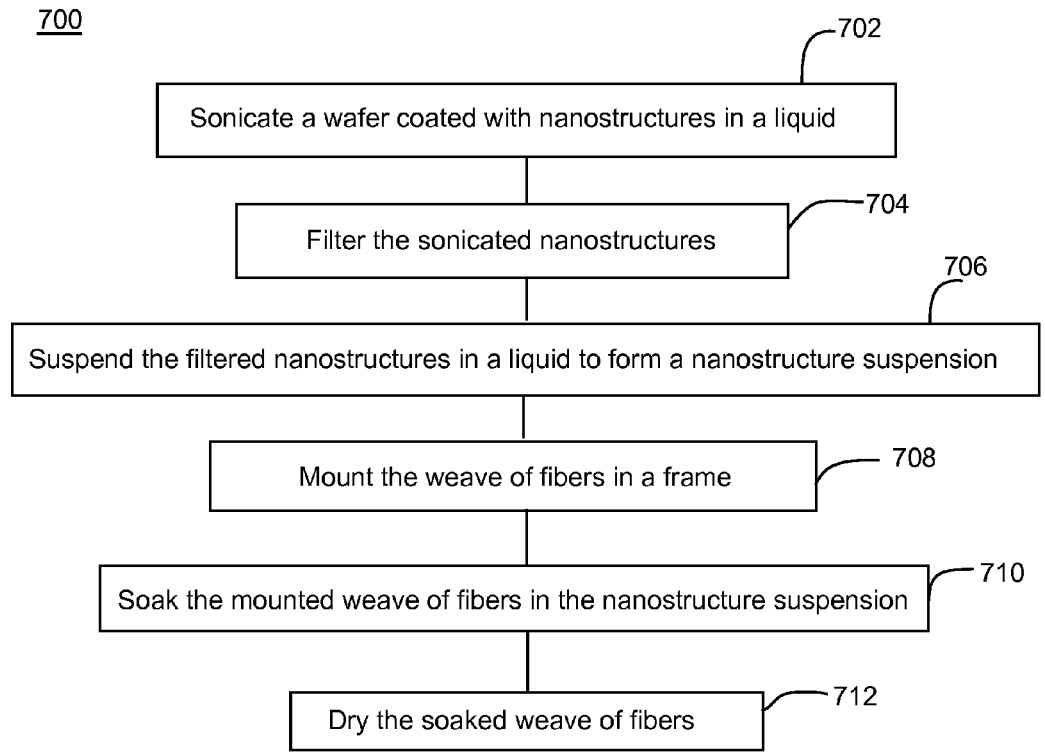
FIG. 7 shows a flowchart providing steps for coating a framed base material with nanofibers, according to an example embodiment of the present invention.
Figure 9:
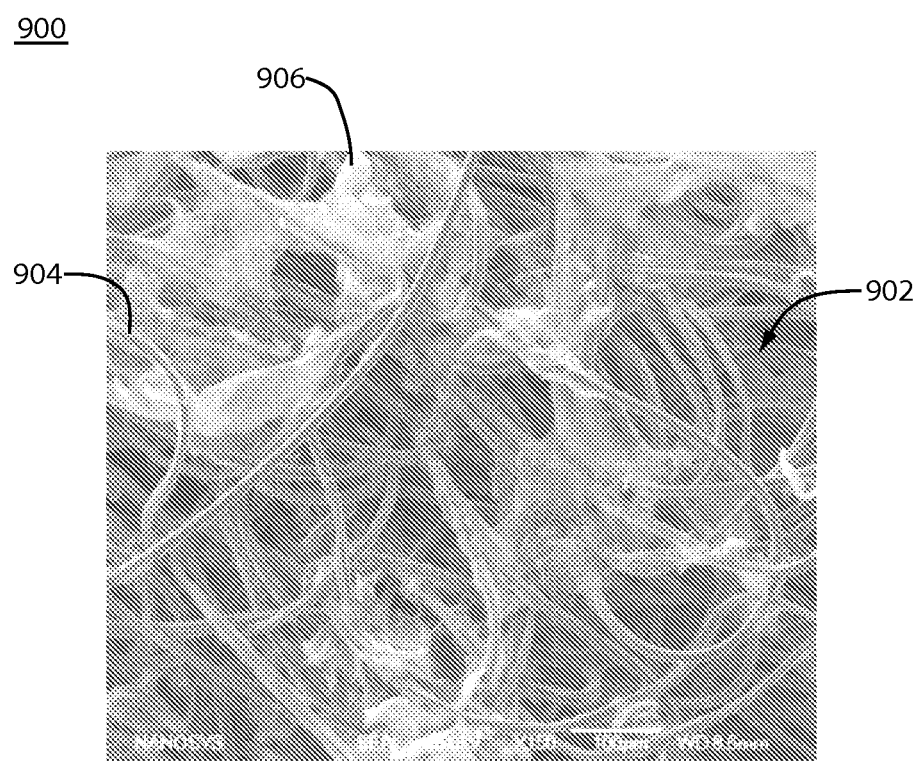
FIGS. 9 and 10 show images of a base structure that was coated with nanofibers in the manner of the flowchart of FIG. 7, according to an example embodiment of the present invention.
Figure 10:
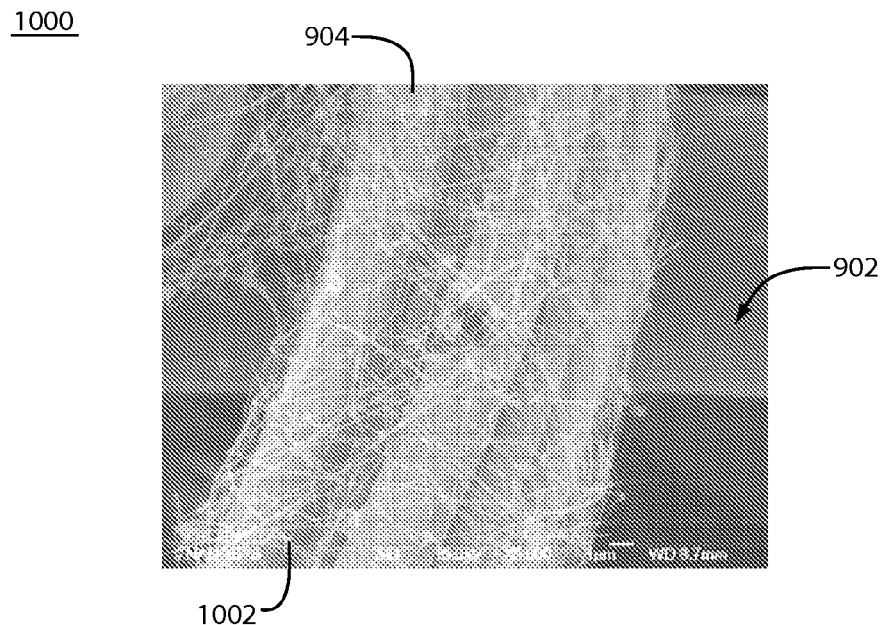

FIGS. 9 and 10 show magnified images 900 and 1000 of a base structure 902 that was coated with nanofibers in a manner similar to flowchart 700 of FIG. 7, according to an example embodiment of the present invention. Images 900 and 1000 were captured by a scanning electron microscope (SEM), where image 900 is a lower magnification relative to image 1000. In FIGS. 9 and 10, base structure 902 is a gauze bandage formed of cotton fiber bundles 904. As shown in FIG. 9, a coating 906 of silica nanofibers on fiber bundles 904 of base structure 902 is somewhat patchy, with nanofibers clumped in various locations. At higher magnification, FIG. 10 shows individual nanofibers 1002 coating fiber bundles 904 in a substantially uniform manner.

The use of charge-based attraction (e.g., electrostatic attraction) to coat a bandage structure or other substrate material with nanostructures according step 600 of FIG. 6 may be accomplished in any manner. In embodiments, the weave of fibers may be positively or negatively charged, to attract nanostructures having an opposite charge to the weave of fibers. For example, step 600 may be performed according to flowchart 1100 of FIG. 11. Flowchart 1100 is described as follows. Note that the steps of flowchart 1100 do not necessarily need to be performed in the order shown, and that not all of the steps shown in FIG. 11 may need to be performed in all situations.

Flowchart 1100 begins with step 1102. In step 1102, the weave of fibers is soaked in a solution containing a positively charged polymer. Any polymer may used in step 1102, including polymers mentioned elsewhere herein or otherwise known. For instance, base structure 300 shown in FIG. 3 may be soaked (e.g., for 30 minutes) in a solution of a positively charged polymer, such as Poly-l-lysine. The positively charged polymer imparts a positive charge to the weave of fibers.

In step 1104, the weave of fibers is washed. The weave of fibers may be washed in any suitable manner and any number of one or more times. Any suitable material may be used to wash base structure 300, including water, isopropanol alcohol, another solution, or other material. In the current example, base structure 300 is removed from the polymer solution, and is washed twice in water and once in isopropanol.

In step 1106, the weave of fibers is dried. The washed base structure 300 may be dried for any length of time, and in any manner, such as by air drying or by application of heat (e.g., flash drying).

In step 1108, a solution containing the nanostructures is applied to the weave of fibers to coat the weave of fibers. The nanostructures in the solution may have a negative charge, and thus are attracted to the weave of fibers due to the imparted positive charge (of step 1102) to coat the weave of fibers. Any suitable solution of nanostructures may be used, including any nanostructure solution described elsewhere herein or otherwise known. For instance, in the current example, an ethanol solution (e.g., 10 milliliters) containing nanofibers is used. The nanostructure solution may be applied to base structure 300 in any manner, including pouring the solution on base structure 300, dipping or depositing base structure 300 in the solution, or in other manner. In the current example, the nanofibers are attracted to base structure 300, coating base structure 300 due to the positive charge of base structure 300.

In step 1110, the coated weave of fibers is incubated. The coated weave of fibers may be incubated in any manner and at any temperature. For instance, in the current example, coated base structure 300 may be incubated at room temperature for 20 minutes.

In step 1112, the coated weave of fibers is dried. The coated weave of fibers may be dried for any length of time, and in any manner, such as by air drying or by application of heat (e.g., flash drying). For instance, in the current example, coated base structure 300 may be dried at 100° C. (e.g., for 10 minutes).

Figure 11:
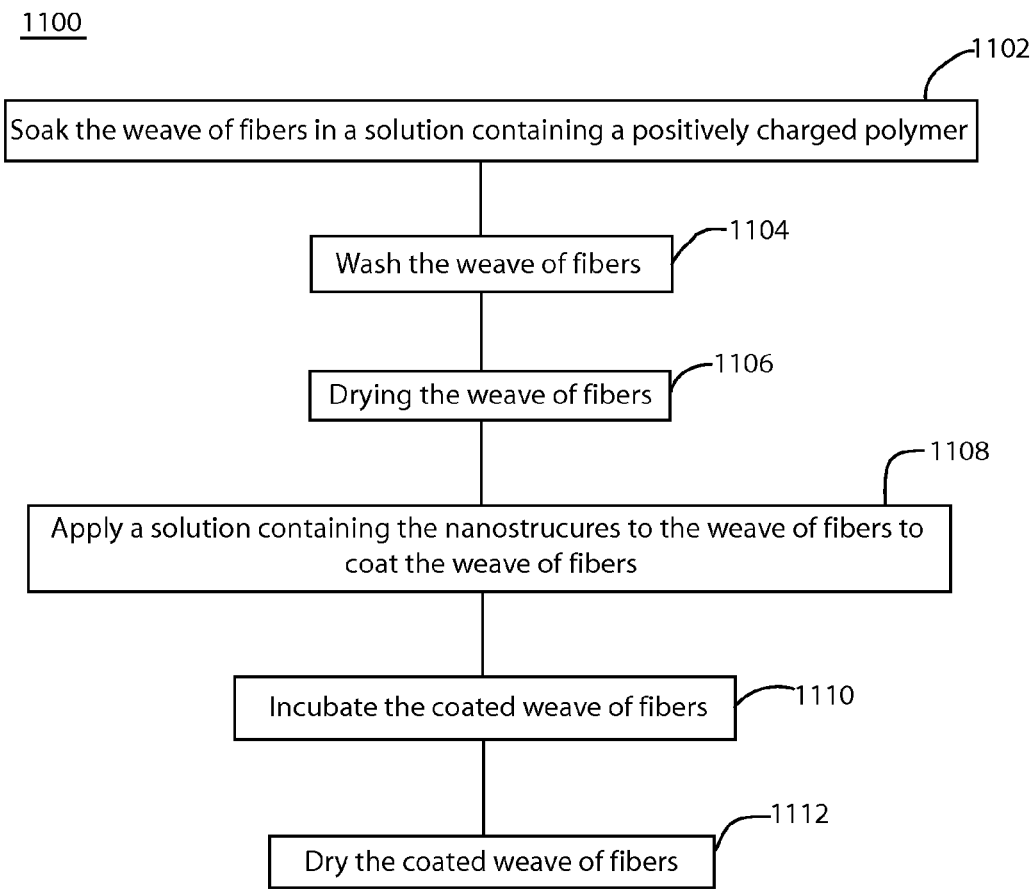
FIG. 11 shows a flowchart providing steps for coating a base material with nanofibers using charge-based attraction, according to an example embodiment of the present invention.
Figure 12:
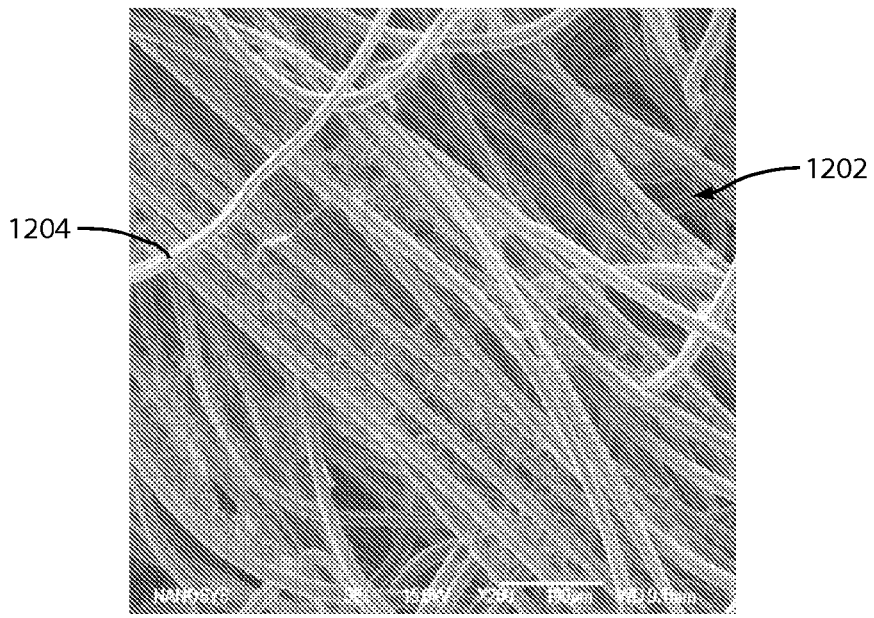
FIGS. 12 and 13 show images of a base structure that was coated with nanofibers in the manner of the flowchart of FIG. 11, according to an example embodiment of the present invention.
Figure 13:
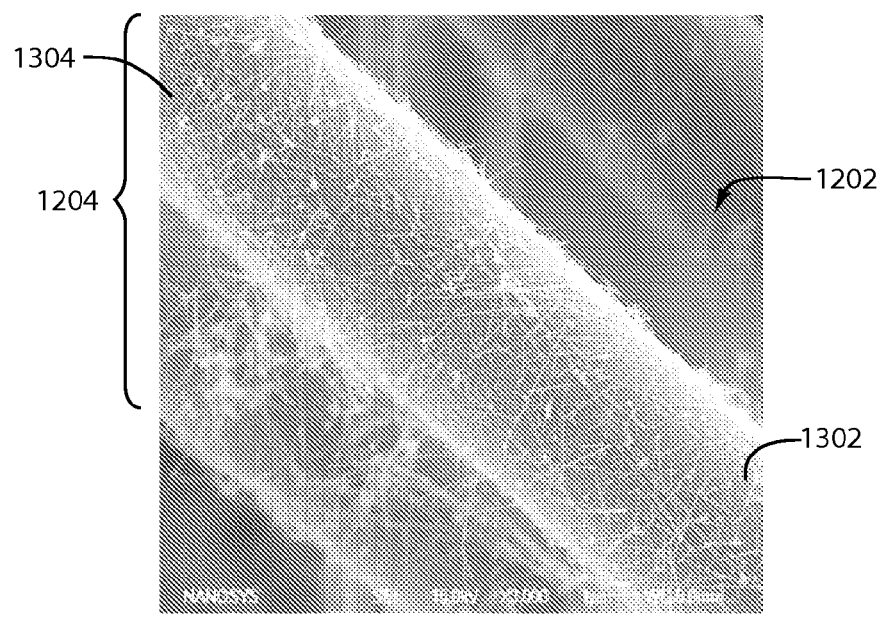

FIGS. 12 and 13 show magnified images 1200 and 1300 of a base structure 1202 that was coated with nanofibers using charge-based attraction in a manner similar to flowchart 1100 of FIG. 11, according to an example embodiment of the present invention. Images 1200 and 1300 were captured by a SEM, and image 1200 is a lower magnification relative to image 1300. In FIGS. 12 and 13, coated base structure 1202 is a gauze bandage formed of cotton fiber bundles 1204. As shown in FIG. 12, fiber bundles 1204 are more evenly coated with nanofibers as compared to fiber bundles 904 in images 900 and 1000 (FIGS. 9 and 10) described above. At higher magnification, FIG. 13 shows individual nanofibers 1302 coating individual fibers 1304 of fiber bundles 1204 in a substantially uniform layer. In addition to achieving a substantially even coating of nanofibers 1302, the resulting coated base structure 1202 has handling properties very similar to untreated cotton gauze. Coated base structure 1202 is very flexible, and extraneous shedding of nanofibers 1302 is not apparent upon handling of coated base structure 1202.

Figures 14, 15:
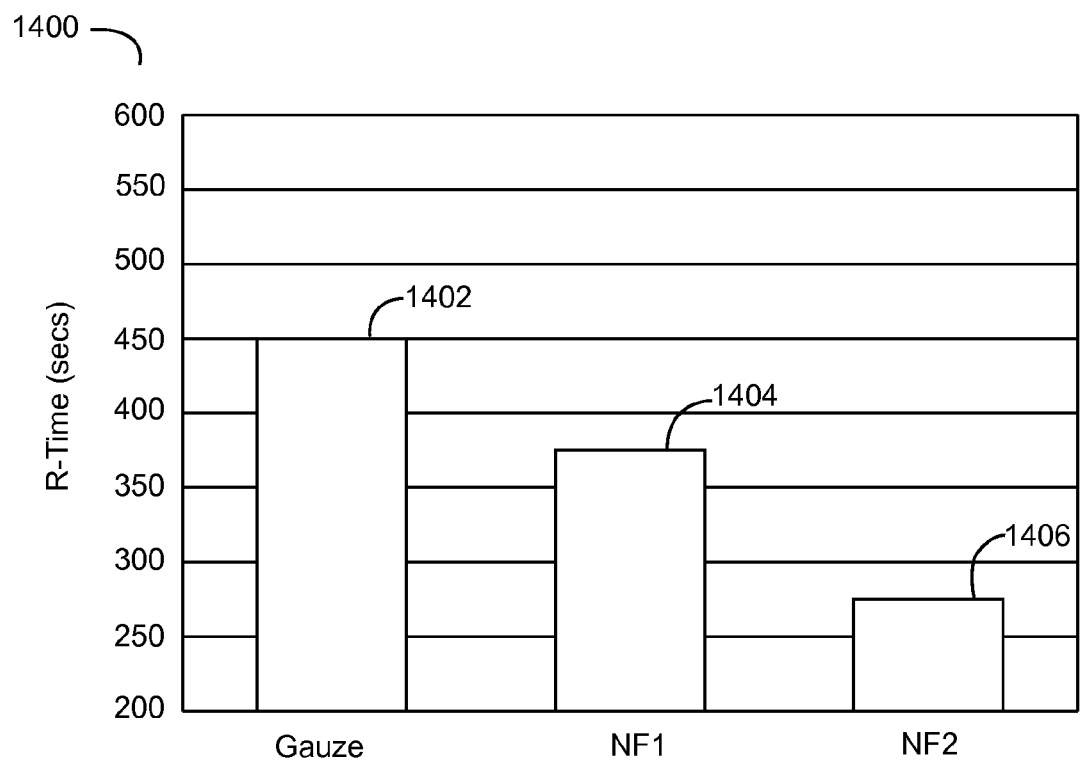
FIG. 14 shows a graph illustrating average times to hemostasis for a conventional cotton gauze bandage and nanofiber coated cotton gauze bandages, according to example embodiments of the present invention.
FIG. 15 shows a process for forming a hemostat, according to an example embodiment of the present invention.

The hemostatic capability of a base structure coated with nanostructures according to embodiments of the present invention may be compared to that of non-nanostructure enhanced bandages. In a first example comparison, a time to initiation of clotting ("R-time") for nanofiber coated base structure 902 (when cotton gauze) was reduced when compared to cotton gauze without a nanofiber coating. Coated base structure 902 initiated clotting in approximately 9 minutes, while the uncoated gauze initiated clotting in approximately 12 minutes. In another example, clotting was initiated for a conventional cotton gauze bandage at an average of approximately 455 seconds, while clotting was initiated for nanofiber coated base structure 902 at an average of approximately 380 seconds, and clotting was initiated for nanofiber coated base structure 1202 in less than 5 minutes (approximately 275 seconds). FIG. 14 shows a graph 1400, illustrating average times to hemostasis for a conventional cotton gauze bandage (plot 1402), for nanofiber coated base structure 902 (cotton gauze bandage in the current example) (plot 1404), and for nanofiber coated base structure 1202 (cotton gauze bandage in the current example) (plot 1406), as determined using a thromboelastograph (TEG). As shown in FIG. 14, according to plot 1402, hemostasis for conventional cotton gauze bandage was measured to occur during a range of approximately 450 to 570 seconds. According to plot 1404, hemostasis for nanofiber coated base structure 902 was measured to occur during a range of approximately 380-390 seconds. According to plot 1406, hemostasis for nanofiber coated base structure 1202 was measured to occur during a range of approximately 275-300 seconds.

The nanofiber coatings of the present invention provide increased platelet binding compared to conventional hemostatic devices, thereby addressing the physiologically relevant response whereby an activated surface triggers the intrinsic coagulation pathway and also leads to enhanced platelet binding. The platelet-binding capability of a base structure coated with nanostructures according to embodiments of the present invention may be compared to that of non-nanostructure enhanced bandages. Experimental results indicate that the nanofiber coating promotes platelet adhesion due to the fact that the chemistry and morphology of the nanofibers are more conducive to platelet binding.

Figure 40:
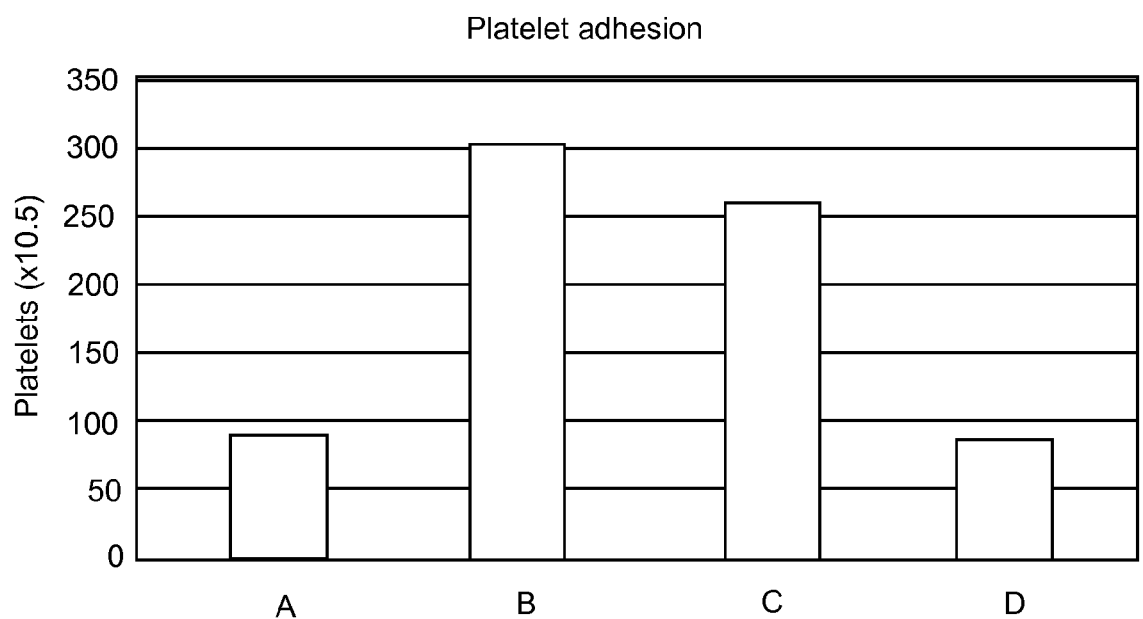
FIG. 40 shows a graph illustrating comparative platelet binding levels for uncoated gauze, conventional Quikclot® Combat Gauze™, and nanofiber coated gauze, according to example embodiments of the present invention.

In a first example comparison involving example embodiments of the present invention, purified gel filtered platelets (GFPs) were prepared from fresh human blood, and pooled GFPs were incubated with base gauze structures for one hour. The base structures were washed and platelet binding was determined using a lactate dehydrogenase (LDH) assay. Nanofiber-coated gauze showed increased binding of platelets when compared to plain gauze or Combat Gauze™. FIG. 40 shows a graph illustrating comparative platelet binding levels for uncoated gauze (sample A), conventional Quikclot® Combat Gauze™ (sample D), and silicon nanofiber coated gauze (sample B with 0.5 mg/cm² nanofiber density, and sample C with 0.25 mg/cm² nanofiber density), according to example embodiments of the present invention. The vertical axis represents the number of adhered platelets ($\times 10.5$). These results indicate a much higher rate of platelet binding (at least a 3- to 4-fold increase) with nanofiber coatings and thus a different, improved mechanism of coagulation compared to conventional hemostatic methods and devices. Without being bound to a particular theory of operation, these results support the concept that nanofibers provide a structural, biomimetic, fibrous scaffold for triggering platelet binding and coagulation. Thus, based on the surprising increase in hemostasis shown with nanofiber coatings and the surprising increase in platelet binding due to such coatings, it is realized that enhanced platelet binding is important for amplifying the coagulation response and increasing clot strength.

Figure 41:
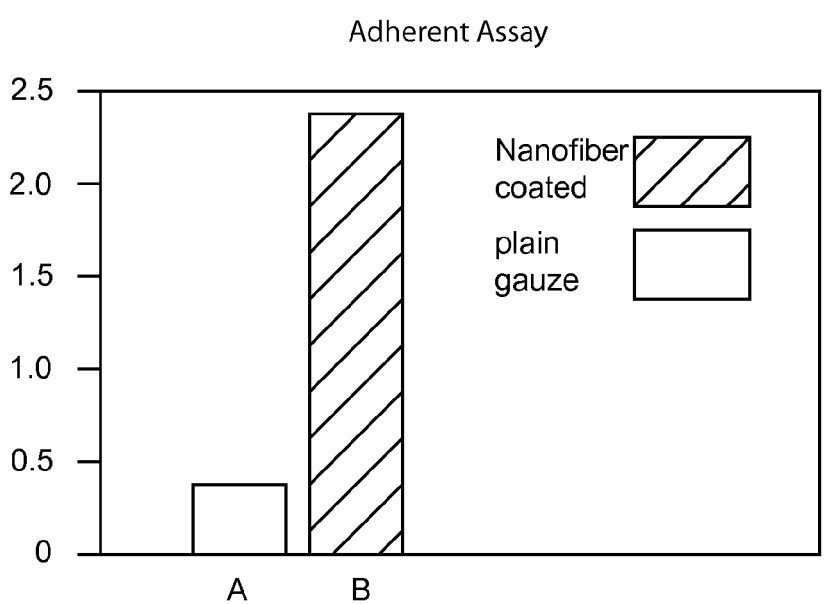
FIG. 41 shows a graph illustrating superior platelet binding of nanofiber-coated gauze compared to uncoated gauze, according to example embodiments of the present invention.
Figure 42:
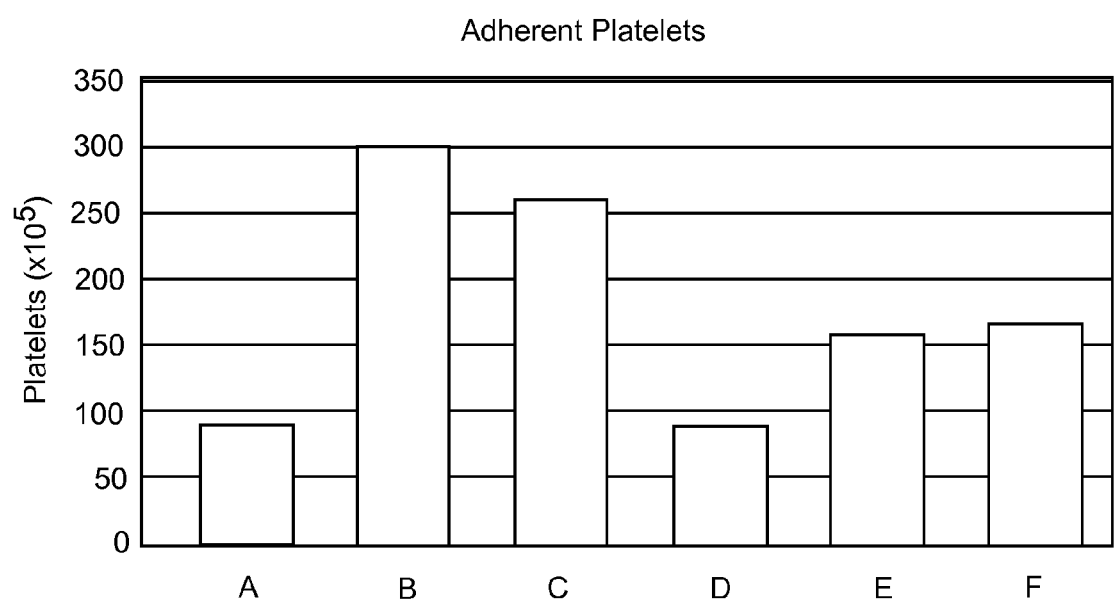
FIG. 42 shows a graph illustrating the superior platelet binding of silicon nanofiber coated gauze and fumed silica-coated gauze, according to example embodiments of the present invention, compared to conventional hemostatic materials (uncoated gauze and Combat Gauze).
Figure 43A:
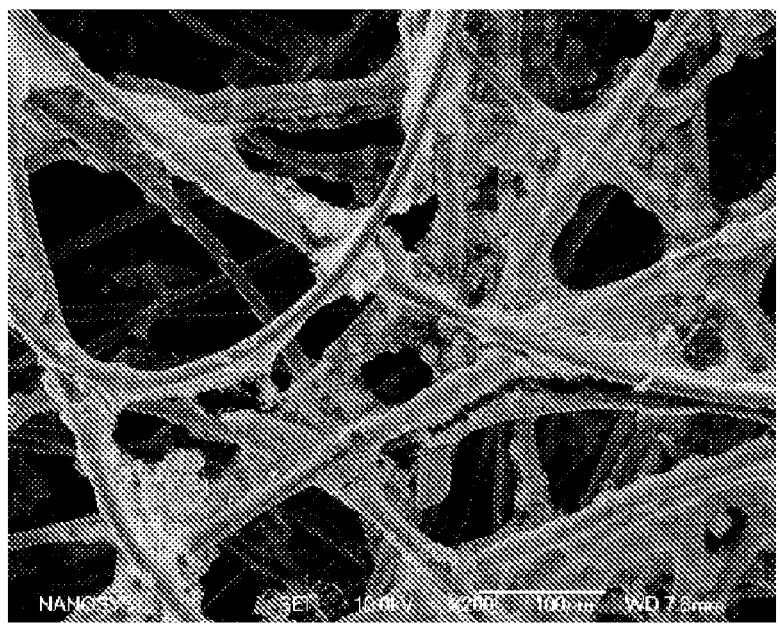
FIGS. 43A-43D show images of silicon nanofiber-loaded CMC scaffolds, according to embodiments of the present invention.
Figure 43B:
Figure 43C:
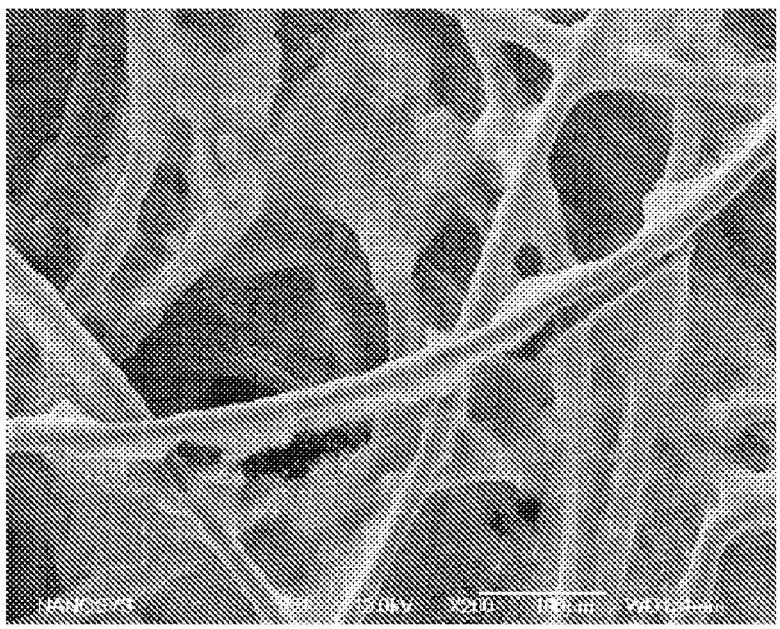
Figure 43D:
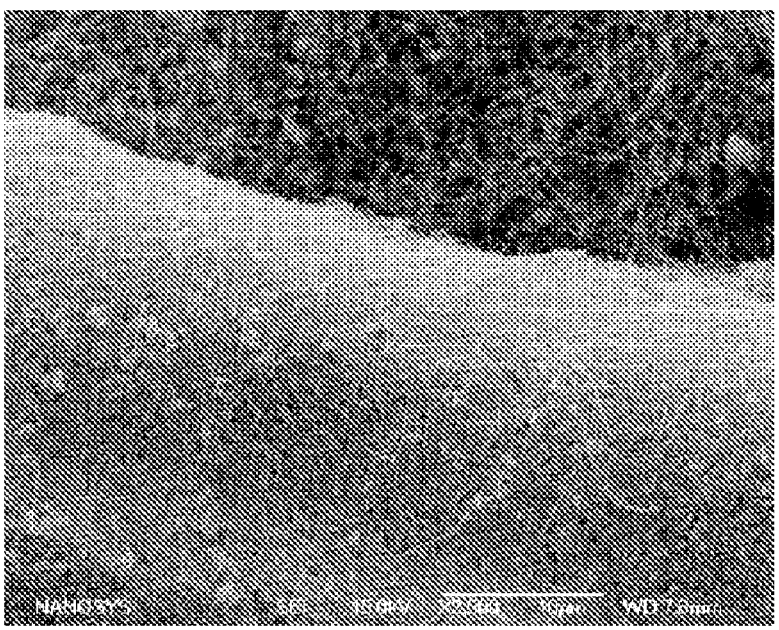

FIG. 41 shows a graph illustrating superior platelet binding of nanofiber-coated gauze compared to uncoated gauze, according to example embodiments of the present invention. In the experiment involving example embodiments of the present invention, $7.1 \times 10^7$ gel-filtered platelets (GFP) were added to gauze and allowed to adhere. Filters with bound platelets were extensively washed and incubated with 1 mL of platelet lysis buffer. Reaction rates for LDH substrate turnover were determined and the background was removed. The adhesion illustrated by the uncoated control gauze (sample A) was $0.328 \pm 0.18$ $A_{450}$ nm/min and the gauze with nanowires (sample B with 0.5 mg/cm$^2$ nanofiber density) was $2.397 \pm 0.079$ $A_{450}$ nm/min. The total platelets bound to the uncoated gauze was $3 \times 10^6$, compared to $1.2 \times 10^7$ platelets bound to the nanofiber-coated gauze, which represents approximately a 4-fold increase in platelet binding with the nanofiber coating. A total of 17% of the platelets bound to the nanofiber-coated gauze. FIG. 42 illustrates the superior platelet binding of silicon nanofiber coated gauze (sample B with 0.5 mg/cm$^2$ nanofiber density, and sample C with 0.25 mg/cm$^2$ nanofiber density) according to example embodiments of the present invention, compared to conventional gauze (sample A—uncoated plain gauze, and sample D—Combat Gauze™). Gauze coated with fumed silica particles (sample E with 0.5 mg/cm$^2$ fumed silica density, and sample F with 0.5 mg/cm$^2$ fumed silica density), according to embodiments of the present invention, also showed improvements in platelet binding compared to conventional gauze, albeit less improvement than silicon nanofiber coated gauze. The vertical axis represents the number of adhered platelets (×10.5). With the nanofiber-coated gauze, approximately 23% and 20.1% of the platelets, respectively, adhered to the nanofiber-coated gauze of samples B and C, respectively, compared to 6.8% for uncoated gauze and 6.6% for Combat Gauze™.

Note that further techniques may be used alternatively to soaking (FIG. 5) and/or charge-based attraction (FIG. 6) to incorporate nanostructures with a substrate material according to step 200 in FIG. 2, including nano-spinning, weaving, and/or further techniques described herein.

In an embodiment, nanostructures may be incorporated with a weave of fibers or other bandage material described elsewhere herein or otherwise known throughout the entire bandage material. In another embodiment, nanostructures may be incorporated with a weave of fibers or other bandage material described elsewhere herein or otherwise known at just a portion of the bandage material. For example, the nanostructures may be incorporated with a bandage material in a pattern (e.g., a surface pattern, a pattern internal to the bandage material). For instance, nanostructures may be incorporated in a portion of a bandage material that is configured to come into contact with a wound when the bandage is applied to a subject, and may not be incorporated in other portions of the bandage material. In another example, nanostructures may be applied to a portion of a closure device that is not within the lumen of a blood vessel. Any suitable pattern of nanostructures may be incorporated with a bandage material or other medical device, including patterns described elsewhere herein.

Example Expandable and Absorbent Hemostatic Material Embodiments

Expandable polymers have been used for wound closure to prevent blood loss after endoscopic surgery where the entry/exit point of the endoscopic device is through a blood vessel. An example of such device is the Angioseal™ vascular closure device sold by St. Jude Medical of St. Paul, Minn. Absorbent materials, such as cotton gauze or tampon structures, have also been used for wound closure. In a device using an expandable material, blood and/or other fluids are absorbed by the material, and the material swells to cause a physical barrier. Static blood may be entrapped within pores of the material, which clots due to stasis. It would be advantageous if the blood within the expanded material could be made to clot more rapidly. Embodiments of the present invention enable an increased rate of clotting for devices based on expandable materials and non-expandable materials (e.g., cotton-based, such as gauze, tampon, and other such non-expanding materials).

In an embodiment, nanostructures, such as nanofibers, are co-formulated with one or more polymers such that the surface of the polymer remains hemostatic—the polymer is not coated so tightly by the nanofibers such that blood cannot access it. Silicon nanowires having an outer core of silicon dioxide are hemostatic due to the procoagulative nature of a negatively charged silicon dioxide surface. By dispersing these nanowires within a material in such a way as to be entrapped by the polymer, but not tightly coating the polymer, an additional surface at which accelerated hemostasis can occur is provided by the nanowires.

FIG. 15 shows a step 1500 for forming a hemostat, according to an example embodiment of the present invention. Step 1500 may be used to form hemostatic structures such as hemostatic bandages or plugs. Further structural and operational embodiments will be apparent to persons skilled in the relevant art(s) based on the discussion regarding step 1500.

Figure 16:
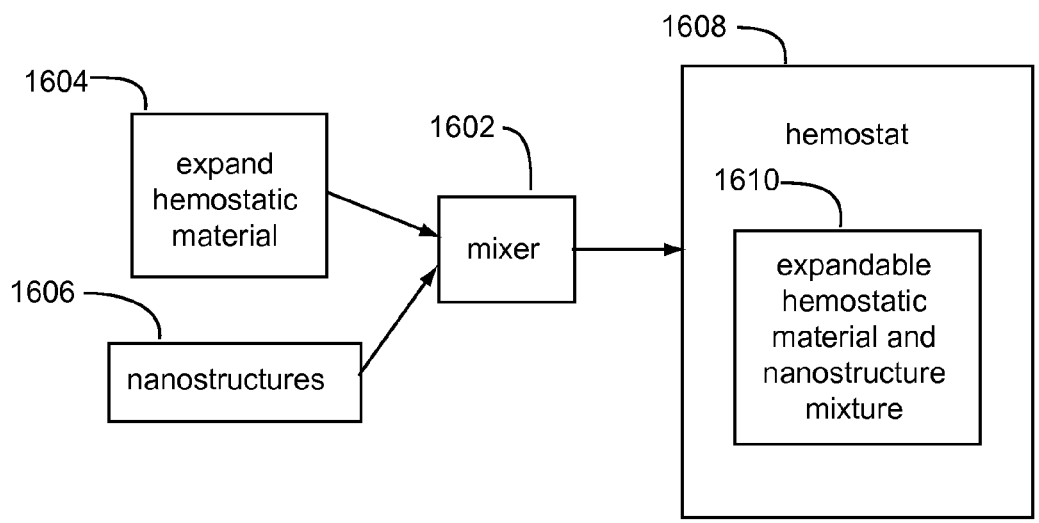
FIG. 16 shows a block diagram of a mixing system, according to an example embodiment of the present invention.

As shown in FIG. 15, in step 1500, an expandable hemostatic material is mixed with a plurality of nanostructures. For example, FIG. 16 shows a block diagram illustrating a mixing system 1600, according to an example embodiment of the present invention. As shown in FIG. 16, a mixer 1602 receives an expandable hemostatic material 1604 and a plurality of nanostructures 1606. Mixer 1602 mixes expandable hemostatic material 1604 and nanostructures 1606 to generate hemostat 1608, which includes an expandable hemostatic material and nanostructure mixture 1610. Mixer 1602 may be any type of mixer, including a vortex mixer, mixing by human/manual effort, or other type of mixer.

Expandable hemostatic material 1604 may be any type of expandable hemostatic material, including gauze (e.g., cotton or other material), a tampon (e.g., cotton or other material), a polymer such as polyethylene glycol (PEG), or other material that expands due to fluid absorption and/or other cause. Nanostructures 1606 may be any type of nanostructure mentioned elsewhere herein or otherwise known. For example, in an embodiment, nanostructures 1606 may include nanowires. The nanowires included in nanostructures 1606 may be similar to nanowire 100 shown in FIG. 1A (a core nanowire structure), or may be core-shell nanowires similar to nanowire 110 of FIG. 1B, having a shell 112 around a nanowire core. When present, shell 112 may be a hemostatic material, such as silicon dioxide.

By mixing nanowires having a hemostatic material shell layer with expandable hemostatic material 1604 using mixer 1602 to form hemostat 1608, an improved hemostatic material is formed over conventional hemostatic materials. Mixer 1602 may be configured to mix nanostructures 1606 and expandable hemostatic material 1604 in a manner (e.g., in a particular ratio) such that nanostructures 1606 are entrapped by expandable hemostatic material 1604, but do not tightly coat expandable hemostatic material 1604. In this manner, an additional surface at which accelerated hemostasis can occur is provided by nanostructures 1606 without blocking the surface of expandable hemostatic material 1604.

Figure 17:
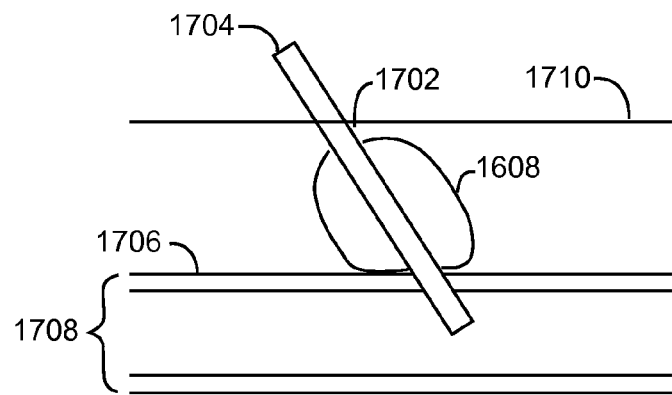
FIG. 17 shows a cross-sectional view of a hemostat inserted in an opening through tissue, according to an example embodiment of the present invention.

Hemostat 1608 can be used to induce clotting by being applied to, or inserted in (e.g., plugging) wounds. For example, FIG. 17 shows a cross-sectional view of hemostat 1608 inserted in an opening 1702 (on a catheter 1704) through tissue 1710, according to an example embodiment of the present invention. For instance, opening 1702 may be formed to enter catheter 1704 in an artery 1708 through an artery wall 1706 during an arteriotomy. Hemostat 1608 may be released from a sheath (not shown in FIG. 17) of catheter 1704 prior to withdrawing catheter 1704 from opening 1702. In an embodiment where expandable hemostatic material 1604 is freeze dried PEG, after being exposed in opening 1702, the porous PEG material of hemostat 1608 rapidly swells by an amount of around 3 to 4 times its original size, such that hemostat 1608 becomes approximately 5% PEG/nanostructures 1606 and 95% blood and other absorbed fluids. When expanded, hemostat 1608 conforms to opening 1702 to provide a seal, and provides hemostasis. Blood collects in hemostat 1608, and clots, providing a platform for natural vessel healing.

In an embodiment, expandable hemostatic material 1604 and nanostructures 1606 are resorbable materials, so that hemostat 1608 is resorbable. Example resorbable materials for expandable hemostatic material 1604 include polymers such as PEG and other resorbable materials mentioned elsewhere herein or otherwise known, and example resorbable nanostructures for nanostructure 1606 include silicon nanowires, including nanowires having a silicon dioxide shell.

Example Hemostatic Material Embodiments

Various materials have been developed to help stop wounds from bleeding excessively and to increase a rate of clotting. Such materials may be used in surgical procedures and/or by first responders to traumatic events, for example. Existing bulk hemostats have disadvantages, however. For example, it would advantageous if existing bulk hemostats functioned more quickly, were resorbable, and/or did not have an exothermic reaction with blood. Embodiments of the present invention overcome these limitations of conventional bulk hemostats.

In an embodiment, nanostructures, such as nanofibers, are co-formulated with glass microspheres (either solid or porous). This co-formulated material has an enhanced hemostatic activity that is not purely additive—i.e., the combination of the nanostructures and glass microspheres has a faster hemostatic activity (e.g., when measured in a TEG) than the nanostructures or glass microspheres alone, which is not necessarily explained purely by a resulting increase in surface area of the hemostat.

Figure 18:
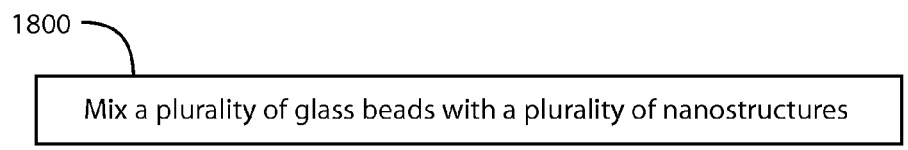
FIG. 18 shows a process for forming a hemostat, according to an example embodiment of the present invention.

FIG. 18 shows a step 1800 for forming a hemostat, according to an example embodiment of the present invention. Step 1800 may be used to form hemostatic materials, such as bulk hemostats, which may be in granular, powder, or other form. Further structural and operational embodiments will be apparent to persons skilled in the relevant art(s) based on the discussion regarding step 1800.

Figure 19:
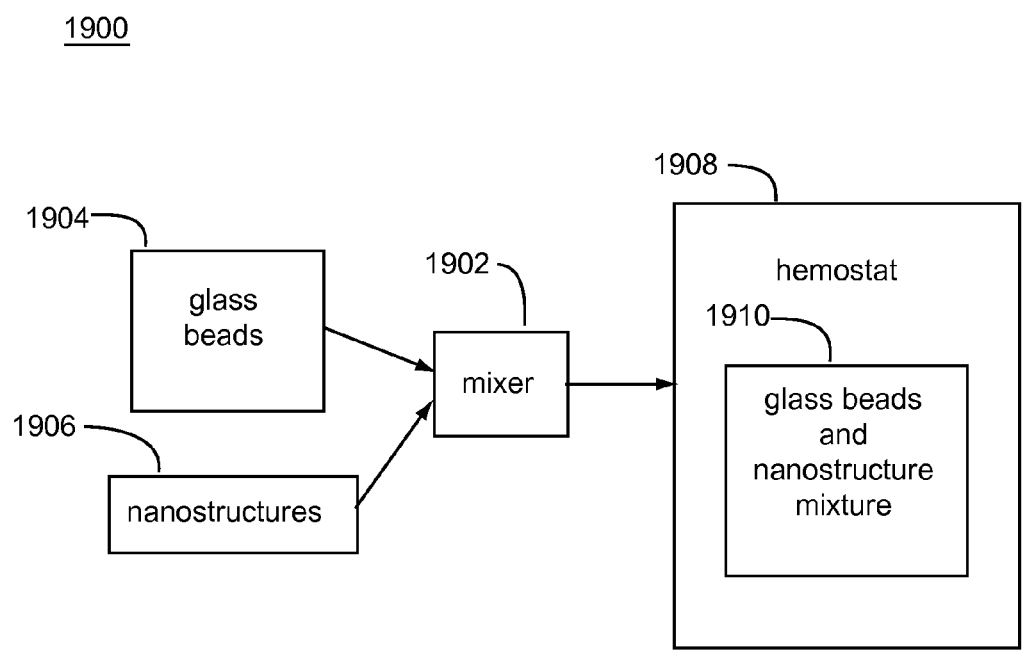
FIG. 19 shows a block diagram of a mixing system, according to an example embodiment of the present invention.

As shown in FIG. 18, in step 1800, a plurality of glass beads is mixed with a plurality of nanostructures. For example, FIG. 19 shows a block diagram illustrating a mixing system 1900, according to an example embodiment of the present invention. As shown in FIG. 19, a mixer 1902 receives glass beads 1904 and a plurality of nanostructures 1906. Mixer 1902 mixes glass beads 1904 and nanostructures 1906 to generate hemostat 1908, which includes a glass bead and nanostructure mixture 1910. Mixer 1902 may be any type of mixer, including a vortex mixer, mixing by manual/human effort, or other type of mixer.

Glass beads 1904 may be solid or porous, and may have any size, including being microspheres. For instance, in an embodiment, glass beads 1904 have diameters in the range of 3-10 micrometers. Nanostructures 1906 may be any type of nanostructure mentioned elsewhere herein or otherwise known. For example, in an embodiment, nanostructures 1906 may include nanowires such as silicon nanowires. The nanowires included in nanostructures 1906 may be similar to nanowire 100 shown in FIG. 1A (a core nanowire structure), or may be core-shell nanowires similar to nanowire 110 of FIG. 1B, having a shell 112 around a nanowire core. When present, shell 112 may be a hemostatic material, such as silicon dioxide.

Hemostat 1908 can be used to induce clotting by being applied to wounds, such as by pouring hemostat 1908 onto/into a wound. By mixing nanowires having a hemostatic material shell layer with glass beads 1904 to form hemostat 1908, an improved hemostatic material is formed over conventional hemostatic materials.

Figure 20:
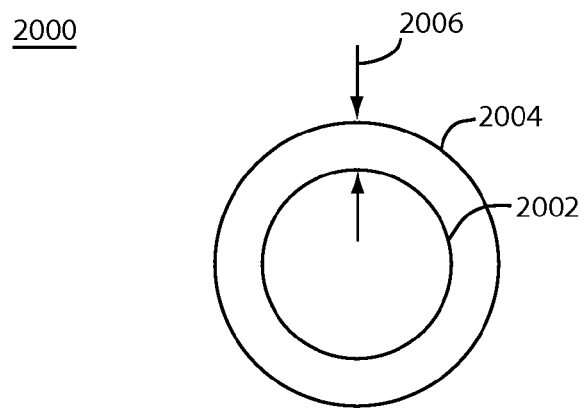
FIG. 20 shows a cross-sectional view of a core-shell particle, according to an example embodiment of the present invention.

As described above, in embodiments, glass beads 1904 may be solid or porous. In further embodiments, glass beads 1904 may be formed from a uniform glass material, or may be core-shell structures, having a core of a first material and a shell layer of a second material. For example, FIG. 20 shows a cross-sectional view of a hemostatic core-shell particle 2000, according to an example embodiment of the present invention. Core-shell particle 2000 has a core portion 2002 surrounded by a shell 2004. Core portion 2002 may have any shape, including being spherical, elongated, irregular, or other shape. Shell 2004 has a thickness 2006. Core portion 2002 and shell 2004 may be made of hemostatic materials to induce coagulation of blood, as described herein. For example, core portion 2002 may be a resorbable polymer, including a copolymer, blend, or other polymer such as lactic acid (e.g., polylactic acid (PLA)), glycolic acid (e.g., polyglycolic acid (PGA)), an amide, an anhydride, an ester, a dioxanone, or other polymer mentioned elsewhere herein or otherwise known. Shell 2004 may be a layer of a hemostatic material, including a glass such as silicon dioxide, a spin-on glass, or other hemostatic material. Alternatively, core portion 2002 may be a glass material, and shell may be a non-glass (e.g., a polymer) material.

Figure 21:
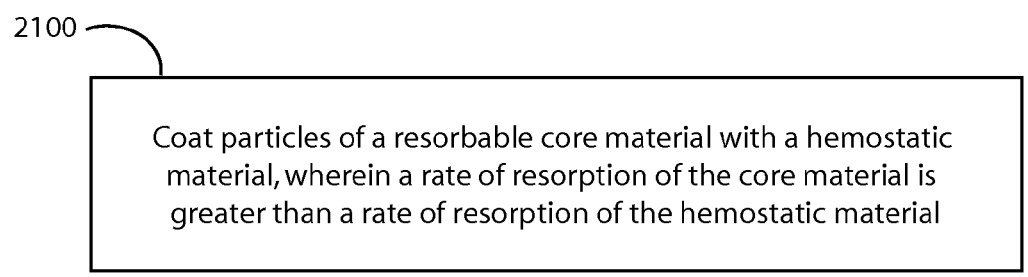
FIG. 21 shows a process for forming a core-shell hemostat, according to an example embodiment of the present invention.

In an embodiment, core-shell particle 2000 may be formed according to step 2100 shown in FIG. 21. In step 2100, particles of a resorbable core material are coated with a hemostatic material, wherein a rate of resorption of the core material is greater than a rate of resorption of the hemostatic material. In such an embodiment, shell 2004 may be selected as a material having greater hemostatic properties than core portion 2002, while core portion 2002 may be selected as a material that has a greater rate of resorption than shell 2004. In this manner, core-shell particle 2000 may be useful at clotting blood (due to shell 2004), while being resorbed by the body faster than conventional hemostatic materials (due to core portion 2002).

For example, shell 2004 may be a glass such as silicon dioxide, a spin-on glass, or other glass or other hemostatic material, which induces clotting upon contact with blood. Core portion 2002 may be a polymer that has a rate of resorption that is greater than a rate of resorption of silicon dioxide, so that an overall rate of resorption of core-shell particle 2000 is increased relative to a solid glass bead (e.g., formed of silicon dioxide). Thickness 2006 of shell 2004 may be tailored to balance the clotting functionality of core-shell particle 2000 (primarily due to shell 2004) with an overall resorption time of core-shell particle 2000 (due to shell 2002 and core portion 2002).

In embodiments, core-shell particle 2000 may be incorporated in (e.g., mixed into) a hemostatic material, such as hemostat 1908 and/or other hemostatic materials/structures described elsewhere herein, along with or in place of nanostructures, glass beads, and/or other particles described herein.

Further Example Hemostatic Bandage Embodiments

As described above, nanostructures may be applied to bandages to assist in activating the intrinsic (contact) clotting cascade, leading to the slowdown or stoppage of bleeding. In embodiments, the nanostructures may be nanoparticles, such as silicon nanoparticles. The nanoparticles may be dispersed in a bandage material to provide enhanced clotting to the bandage material.

Figure 22:
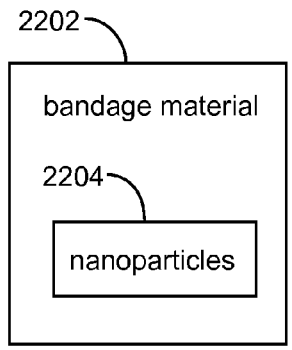
FIGS. 22 and 23 show block diagrams of hemostatic bandages, according to example embodiments of the present invention.

For example, FIG. 22 shows a block diagram of a hemostatic bandage 2200, according to an example embodiment of the present invention. As shown in FIG. 22, hemostatic bandage 2200 includes a bandage material 2202 and a plurality of nanoparticles 2204 (which may collectively be referred to as a "nanopowder"). Bandage material 2202 may be any bandage material described elsewhere herein, including resorbable and/or non-resorbable substrate materials such as organic materials, inorganic materials, woven materials/fabrics, nonwoven materials/fabrics (e.g., nonwoven fiber materials such as a cotton ball), synthetic materials (e.g., rayon, nylon/lycra, Gore-Tex®, polymers, etc.), natural materials (e.g., cotton), biologics/biological derived materials (e.g., chitosan, including chitosan microparticles, collagen, gelatin, cellulose, etc.), and/or particles (e.g., glass or polymer beads).

Figure 23:
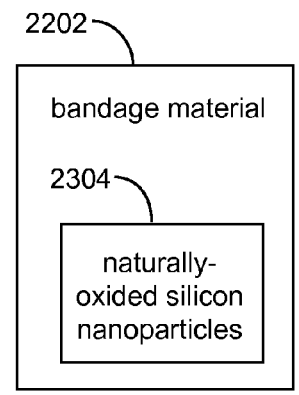

Nanoparticles 2204 may be any type of nanoparticles, such as silicon nanoparticles, for example. Such nanoparticles may have an outer thin oxide layer, which may be naturally occurring. For example, FIG. 23 shows a block diagram of hemostatic bandage 2200 of FIG. 22, where nanoparticles 2204 are naturally-oxidized silicon nanoparticles 2302. Naturally-oxidized silicon nanoparticles 2302 have an outer thin oxide layer that is formed by the natural oxidation of silicon nanoparticles (e.g., due to the exposure to air or other oxygen-containing environment). Naturally-oxidized silicon nanoparticles 2302 may perform better as a hemostatic material (e.g., may be more glass-like) as compared to fumed silica (which is completely oxidized silicon particles), because the thin oxide layer is absorbed by the human body to which bandage material 2202 is applied, exposing the underlying silicon material of naturally-oxidized silicon nanoparticles 2302 to the human body, which may be important in inducing the clotting effect.

Figure 24:
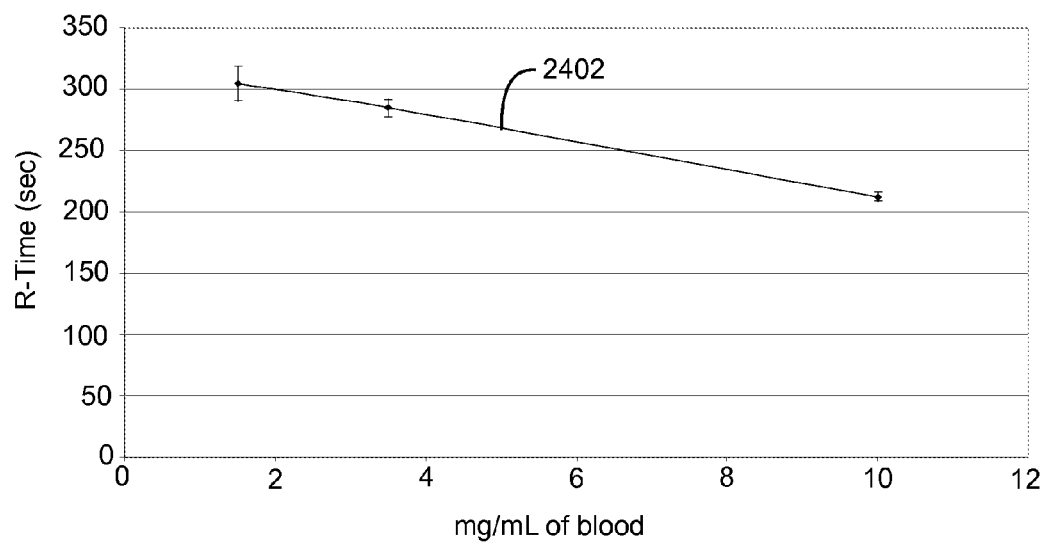
FIG. 24 shows a graph of clot time in the presence of a silicon nanopowder, according to an example embodiment of the present invention.

For instance, FIG. 24 shows a graph 2400 of clot time for a bandage containing a silicon nanopowder, according to an example embodiment of the present invention. The data of graph 2400 was obtained using a thromboelastograph (TEG), for a bandage that included commercial silicon nanopowder (manufactured by laser decomposition) that included nanoparticles having an average particle size of approximately 50 nm. As shown in FIG. 24, R-time (in seconds) is plotted on the Y-axis versus an amount of blood (in milligram/milliliter or mg/mL). A plot line 2402 in graph 2400 indicates that at approximately 1.8 mg/mL, the R-time is approximately 310 seconds, at approximately 3.8 mg/ML, the R-time is approximately 280 seconds, and at approximately 10 mg/mL, and the R-time is approximately 210 seconds (plot line 2402 is a continuous line connected between these points in graph 2400). While the indicated clot time in the presence of silicon nanopowder is in the range of approximately 210 seconds to 310 seconds, when silicon nanopowder is not present, a bandage has an R-time of approximately 800 seconds. Thus, the addition of a silicon nanopowder to a bandage forms a hemostat with substantially faster clotting time than bandages without a hemostat.

Silicon nanoparticles (e.g., silicon particles of less than about 100 nm in diameter) may have a same hemostatic efficacy as silicon nanowires based on preliminary testing results. Based on TEG testing results, fumed silica is determined to not perform as well as silicon nanowires in initiating the clotting cascade in vitro. Thus, silicon nanoparticles and silicon nanowires, which both have a thin oxide layer, are preferable to fumed silica.

Figure 25:
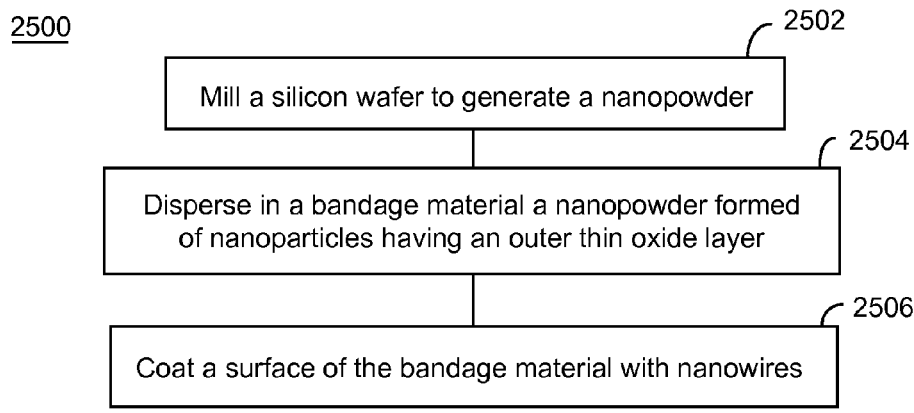
FIG. 25 shows a flowchart for forming a hemostatic bandage, according to an example embodiment of the present invention.
Figure 26:
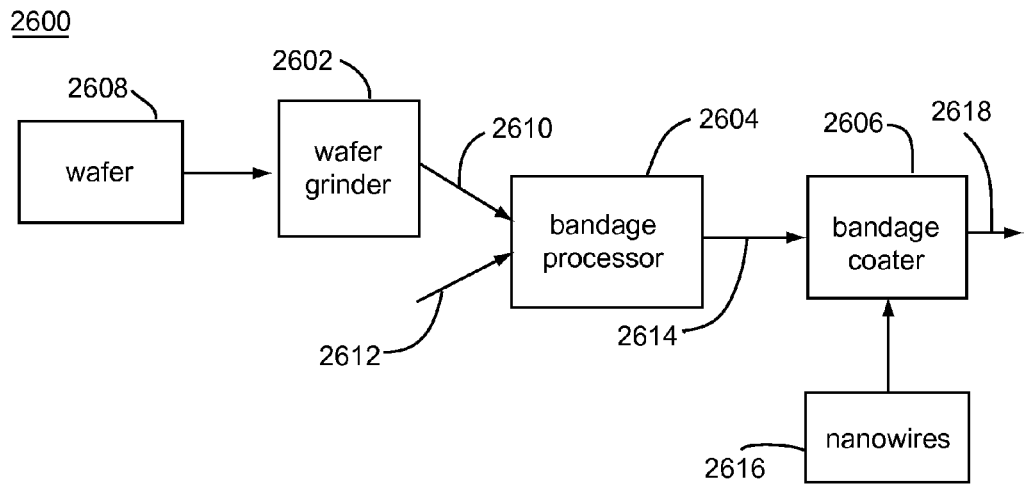
FIG. 26 shows a block diagram of a hemostatic bandage fabrication system, according to an embodiment of the present invention.

Hemostatic bandage 2200 may be formed in any manner. For instance, FIG. 25 shows a flowchart 2500 for forming a hemostatic bandage, according to an example embodiment of the present invention. Various systems may be configured to perform flowchart 2500 to form a hemostatic bandage 2200. For example, FIG. 26 shows a block diagram of a hemostatic bandage fabrication system 2600, according to an embodiment of the present invention. As shown in FIG. 26, system 2600 includes a wafer grinder 2602, a bandage processor 2604, and a bandage coater 2606. Flowchart 2500 is described with respect to system 2600 for purposes of illustration. Note that not all of the steps shown in FIG. 25 need to be performed in all embodiments. Flowchart 2500 is described as follows.

Flowchart 2500 begins with step 2502. In step 2502, a silicon wafer is milled to generate a nanopowder. For instance, wafer grinder 2602 shown in FIG. 26 may be configured to perform step 2502. As shown in FIG. 26, wafer grinder 2602 receives wafer 2608, which may be a silicon wafer. Wafer grinder 2602 is configured to grind wafer 2608 according to any suitable grinding process, including milling wafer 2608 (e.g., using a physical milling mechanism, jet milling, etc.), applying laser decomposition to wafer 2608, or any other suitable technique. In the current example, wafer grinder 2602 generates a silicon nanopowder 2610.

In an embodiment, silicon nanopowder 2610 is naturally oxidized by exposure to the air or other oxygen containing environment. The natural oxidation of silicon nanopowder 2610 creates a thin oxide layer on the silicon nanoparticles of silicon nanopowder 2610 (e.g., creating naturally-oxidized silicon nanoparticles 2302 shown in FIG. 23). Alternatively, silicon nanopowder 2610 may be thermally oxidized to create a thin oxide layer on the nanoparticles of silicon nanopowder 2610, or may be oxidized (naturally or thermally) such that the nanoparticles are fully oxidized into fumed silica nanoparticles.

In step 2504, a nanopowder formed of nanoparticles having an outer thin oxide layer is dispersed in a bandage material. For example, bandage processor 2604 shown in FIG. 26 may be configured to perform step 2504. As shown in FIG. 26, bandage processor 2604 receives silicon nanopowder 2610 and a bandage material 2612. Bandage material 2612 may include completed bandages or may include materials used to create bandages, include any of the bandage materials described elsewhere herein or otherwise known. Bandage processor 2604 may be configured to disperse silicon nanopowder 2610 into the completed bandages of bandage material 2612, or may be configured to fabricate bandages that include silicon nanopowder 2610 dispersed therein.

For example, in an embodiment where bandage processor 2604 receives completed bandages, silicon nanopowder 2610 may be poured or injected onto the completed bandages in a solid form or in the form of a liquid having silicon nanopowder 2610 dissolved therein (e.g., flowed through the bandages, leaving silicon nanopowder 2610 embedded in the bandages). In an embodiment where bandage processor 2604 receives bandage materials, silicon nanopowder 2610 may be applied to the bandage materials (e.g., coated onto, flowed through, mixed into, etc.), and the bandage materials may be subsequently fabricated into completed bandages by bandage processor 2604. Persons skilled in the relevant art(s) will know how to configure bandage processor 2604 to fabricate bandages from bandage materials (e.g., by weaving fibers into bandages, etc.). As shown in FIG. 26, bandage processor 2604 generates hemostatic bandages 2614.

As described above, silicon nanopowder 2610 in hemostatic bandages 2614 increases a rate of blood clotting for hemostatic bandages 2614 relative to bandages that do not include a hemostatic element. Furthermore, silicon nanopowder 2610 is resorbable, and thus does not have to be subsequently manually removed from a human subject. When silicon nanopowder 2610 includes silicon nanoparticles having a thin-oxide layer, silicon nanopowder 2610 may perform better as a hemostatic material as compared to fumed silica. This may be because the thin oxide layer is absorbed by the human body to which hemostatic bandages 2614 are applied, exposing the underlying silicon material of silicon nanopowder 2610 to the human body, which may induce the clotting effect.

Figure 27:
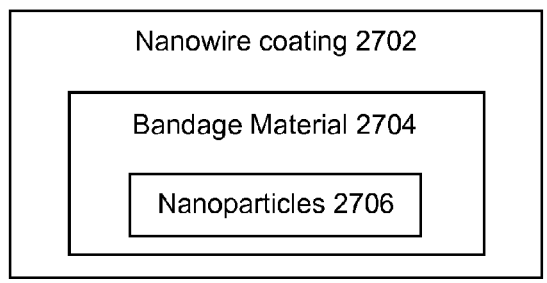
FIG. 27 shows a block diagram cross-sectional view of a nanowire-coated hemostatic bandage, according to an example embodiment of the present invention.

In step 2506, a surface of the bandage material is coated with nanowires. Step 2506 is optional. In an embodiment, bandage coater 2606 shown in FIG. 26, bandage coater 2606 receives hemostatic bandages 2614 and nanowires 2616. For example, nanowires 2616 may include silicon nanowires, potassium nanowires, silicon nanowires functionalized with potassium, silicon nanowires having an outer layer of silicon dioxide, and/or other type of nanowire described elsewhere herein or otherwise known. Bandage coater 2606 is configured to coat hemostatic bandages 2614 with nanowires 2616 to generate nanowire-coated hemostatic bandages 2618. For instance, FIG. 27 shows a block diagram of a cross-sectional view of a nanowire-coated hemostatic bandage 2700, which is an example bandage of nanowire-coated hemostatic bandages 2618, according to an embodiment. As shown in FIG. 27, nanowire-coated hemostatic bandage 2700 includes a nanowire coating 2702, a bandage material 2704, and nanoparticles 2706. Bandage material 2704 contains nanoparticles 2706 of nanopowder 2610. Nanowire coating 2702 is a coating of nanowires 2616 over a surface of bandage material 2704.

Bandage coater 2606 may be configured to coat a portion of all of a surface of hemostatic bandages 2614 with nanowires 2616 in any suitable manner, including as described above with respect to step 200 in FIG. 2, step 500 in FIG. 5, step 600 in FIG. 6, flowchart 700 in FIG. 7, or flowchart 1100 in FIG. 11, where weaves of fibers are coated with nanostructures. For example, bandage coater 2606 may spray nanowires 2616 onto hemostatic bandages 2614 in solid or liquid form, may pour spray nanowires 2616 onto hemostatic bandages 2614 in liquid form, may soak hemostatic bandages 2614 in a solution that contains nanowires 2616, etc. In an embodiment, hemostatic bandages 2614 may have a charge (either positive or negative) imparted thereon, while nanowires 2616 may be imparted with an opposite charge, which causes nanowires 2616 to be attracted to hemostatic bandages 2614, in a similar manner as described elsewhere herein.

Nanowires 2616 coating nanowire-coated hemostatic bandages 2618 increase a rate of blood clotting relative to bandages that do not include a hemostatic element. Furthermore, nanowires 2616 may have a higher tissue adhesion ability relative to nanopowder 2610, thus enhancing tissue adhesion by nanowire-coated hemostatic bandages 2618. Furthermore, silicon nanowires 2616 are resorbable, and thus do not have to be subsequently manually removed from a human subject. Still further, the combination of nanowires 2616 and silicon nanopowder 2610 in nanowire-coated hemostatic bandages 2618, as described above, may reduce a cost of bandages relative to bandages that include nanowires 2616 throughout, because nanowires 2616 are more expensive than silicon nanopowder 2610.

One possible mechanism for a hemostatic action that may be provided/enhanced by nanowire-coated hemostatic bandages 2618 is described as follows: A nanowire-coated hemostatic bandage 2618 is applied to a wound. Nanowires 2616 coating nanowire-coated hemostatic bandage 2618 increase adhesion to the wound. Blood from the wound comes into contact with nanowires 2616, and is drawn into nanowire-coated hemostatic bandage 2618, which may be porous. An intrinsic coagulation pathway is triggered by the binding of high-molecular-wt kininogen (HMWK) to the surface of nanowires 2616 (which may be negatively charged). The intrinsic coagulation cascade proceeds, and is amplified by the presence of nanowires 2616. Thrombin is activated, and a fibrin clot is formed that integrates within a mesh of nanowires 2616. A binding and aggregation of platelets occurs, which completes formation of the clot. An overall rate of the coagulation and a strength of the clot is aided by nanowires 2616. In this manner, hemostasis is achieved.

Note that this example possible mechanism for hemostatic action that may be provided/enhanced by nanowire-coated hemostatic bandages 2618 is provided for purposes of illustration, and is not intended to be limiting. Further mechanisms and/or variations of this illustrated mechanism may alternatively be performed by nanowire-coated hemostatic bandages 2618.

Example Hemostatic Material Embodiments with Multiple Lengths of Nanowires

As described above, nanowires may be applied to bandages to assist in activating the intrinsic (contact) clotting cascade, leading to the slowdown or stoppage of bleeding. In embodiments, nanowires of different lengths may be applied to bandages to tailor the clotting and tissue adhesion characteristics of the bandages. Any number of different lengths of nanowires may be applied to bandages to tailor the clotting and tissue adhesion characteristics.

Shorter nanowires penetrate more deeply and provide extra surface area for enhanced clotting. Longer nanowires tend to remain at the bandage surface, where they assist in adhesion to tissue. Relatively longer nanowires demonstrate better adhesion properties than do shorter nanowires. Shorter nanowires, however, are more easily incorporated at high concentrations into bandage materials, because longer nanowires tend to be filtered by the bandage material and remained largely on the surface of the bandage material. The presence of longer nanowires at the bandage surface is beneficial for imparting adhesive properties to the bandage, but such filtering makes it difficult to achieve nanowire concentrations in the bandage that are optimal for accelerating clotting using longer nanowires alone.

In an embodiment, both short and long nanowires may be dispersed in a bandage to optimize separately both adhesion and clotting acceleration. For example, an optimized ratio of concentrations of short and long nanowires may be added homogeneously to a bandage, or the short and long nanowires may be spatially separated in the bandage to optimize a hemostatic efficacy. For example, it may be beneficial to position a high concentration of shorter nanowires in a center of the bandage, and to position longer nanowires around a periphery of the bandage. This arrangement can be used to form a seal with tissue at the perimeter edges of the bandage where the longer nanowires are concentrated, and may enable a clotting rate to be optimized directly over the wound (adjacent to a central region of the bandage where shorter nanowires are concentrated). Any arrangement of nanowires may be formed, including forming concentric rings of short and long nanowires radiating from the center of the bandage, for example.

Figure 28:
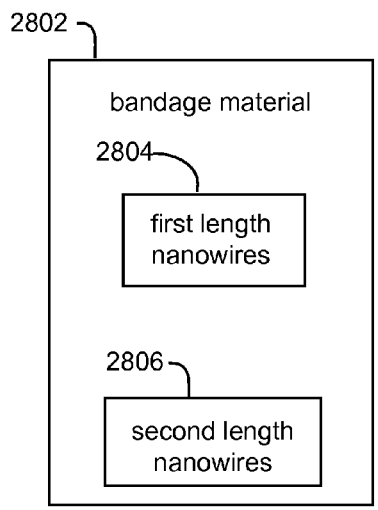
FIG. 28 shows a block diagram of a hemostatic bandage that includes multiple lengths of nanowires, according to an example embodiment of the present invention.

For example, FIG. 28 shows a block diagram of a hemostatic bandage 2800 that includes multiple lengths of nanowires, according to an example embodiment of the present invention. As shown in FIG. 28, hemostatic bandage 2800 includes a bandage material 2802, a plurality of nanowires of nanowires of a first length 2804, and a plurality of nanowires of a second length 2806. Bandage material 2802 may be any bandage material described elsewhere herein, including resorbable and/or non-resorbable substrate materials such as organic materials, inorganic materials, woven materials/fabrics, nonwoven materials/fabrics (e.g., nonwoven fiber materials such as a cotton ball), synthetic materials (e.g., rayon, nylon/lycra, Gore-Tex®, polymers, etc.), natural materials (e.g., cotton), biologics/biological derived materials (e.g., chitosan, including chitosan microparticles, collagen, gelatin, etc.), and/or particles (e.g., glass or polymer beads).

First length nanowires 2804 includes nanowires formed to each have a first length. Second length nanowires 2806 includes nanowires formed to each have a second length. The second length of second length nanowires 2806 is greater than the first length of first length nanowires 2804.

Figure 29:
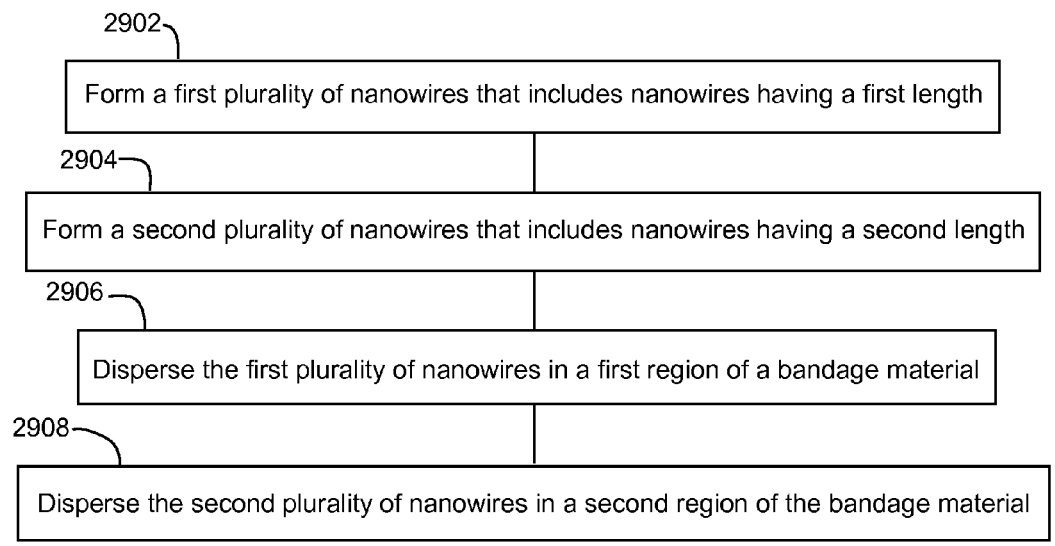
FIG. 29 shows a flowchart for forming a hemostatic bandage having multiple lengths of nanowires, according to an example embodiment of the present invention.
Figure 30:
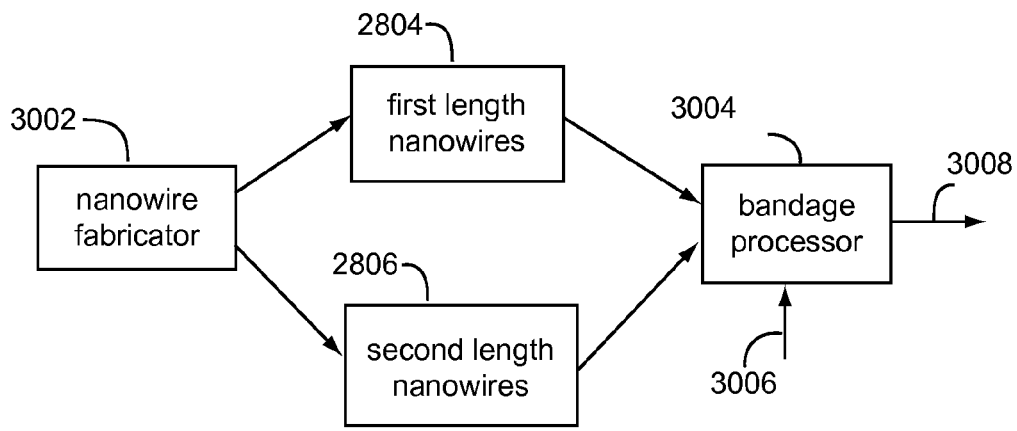
FIG. 30 shows a block diagram of a hemostatic bandage fabrication system, according to an embodiment of the present invention.

Hemostatic bandage 2800 may be formed in any manner. For instance, FIG. 29 shows a flowchart 2900 for forming a hemostatic bandage having multiple lengths of nanowires, according to an example embodiment of the present invention. Various systems may be configured to perform flowchart 2900 to form hemostatic bandage 2800. For example, FIG. 30 shows a block diagram of a hemostatic bandage fabrication system 3000, according to an embodiment of the present invention. As shown in FIG. 30, system 3000 includes a nanowire fabricator 3002 and a bandage processor 3004. Flowchart 2900 is described with respect to system 3000 for purposes of illustration. Note that not all of the steps shown in FIG. 29 need to be performed in all embodiments, and the steps of flowchart 2900 do not necessarily need occur in the order shown. Flowchart 2900 is described as follows.

Flowchart 2900 begins with step 2902. In step 2902, a first plurality of nanowires is formed that includes nanowires having a first length. For example, nanowire fabricator 3002 shown in FIG. 30 may be configured to perform step 2902. As shown in FIG. 30, nanowire fabricator 3002 generates first length nanowires 2804. Nanowire fabricator 3002 may be configured to generate first length nanowires 2804 according to any suitable nanowire fabrication technique described or referenced herein, or otherwise known. Nanowire fabricator 3002 generates first length nanowires 2804 to have a relatively short length, such as having lengths in the range of <1 nm to about 500 nm.

In step 2904, a second plurality of nanowires is formed that includes nanowires having a second length. For example, nanowire fabricator 3002 shown in FIG. 30 may also be configured to perform step 2904. As shown in FIG. 30, nanowire fabricator 3002 generates second length nanowires 2806. Nanowire fabricator 3002 may be configured to generate second length nanowires 2806 according to any suitable nanowire fabrication technique described or referenced herein, or otherwise known. Nanowire fabricator 3002 generates second length nanowires 2806 to have a relatively longer length, such as having lengths in the range of 20 to 30 microns. For example, longer nanowires may be generated by nanowire fabricator 3002 by allowing a longer nanowire growth time relative to a growth time for shorter nanowires (in step 2902), or by other suitable technique.

In step 2906, the first plurality of nanowires is dispersed in a first region of a bandage material. For example, bandage processor 3004 may be configured to perform step 2906. As shown in FIG. 30, bandage processor 3004 receives first length nanowires 2804, second length nanowires 2806, and a bandage material 3006. Bandage material 3006 may include completed bandages or may include materials used to create bandages, include any of the bandage materials described elsewhere herein or otherwise known. Bandage processor 3004 may be configured to disperse first length nanowires 2804 into a first region of the completed bandages of bandage material 3006, or may be configured to fabricate bandages that include first length nanowires 2804 dispersed in the first region.

For example, in an embodiment where bandage processor 3004 receives completed bandages, first length nanowires 2804 may be poured or injected onto the completed bandages in a solid or liquid form (e.g., a liquid including first length nanowires 2804 may be flowed through the bandages, leaving first length nanowires 2804 embedded in the first region of the bandages). In an embodiment where bandage processor 3004 receives bandage materials, first length nanowires 2804 may be applied to the first region of the bandage materials (e.g., coated onto, flowed through, etc.), and the bandage materials may be subsequently fabricated into completed bandages by bandage processor 3004. Persons skilled in the relevant art(s) will know how to configure bandage processor 3004 to fabricate bandages from bandage materials (e.g., by weaving fibers into bandages, etc.).

In step 2908, the second plurality of nanowires is dispersed in a second region of the bandage material. For example, bandage processor 3004 may be configured to perform step 2908. Similarly to step 2906, bandage processor 3004 may be configured to disperse nanowires of a second length 2806 into a second region of the completed bandages of bandage material 3006, or may be configured to fabricate bandages that include nanowires of a second length 2806 dispersed in the second region.

In a similar fashion as described above, second length nanowires 2806 may be poured or injected onto completed bandages in a solid or liquid form. In an embodiment where bandage processor 3004 receives bandage materials, second length nanowires 2806 may be applied to the second region of the bandage materials (e.g., coated onto, flowed through, etc.), and the bandage materials may be subsequently fabricated into completed bandages by bandage processor 3004. As shown in FIG. 26, bandage processor 3004 generates a hemostatic bandage 2800.

Figure 31:
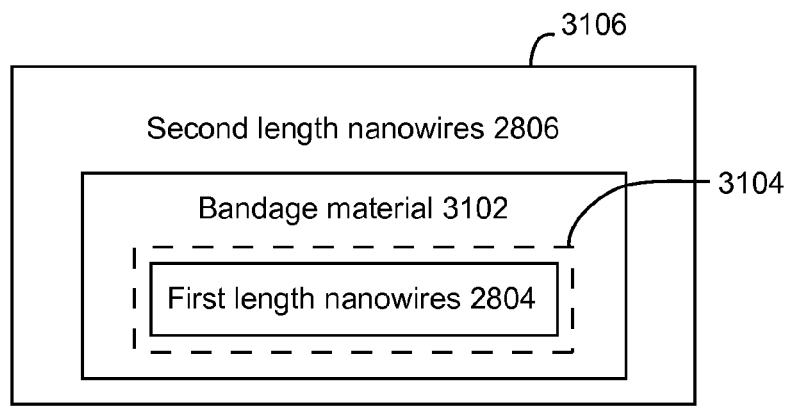
FIG. 31 shows a block diagram cross-sectional view of a hemostatic bandage, according to an embodiment of the present invention.

In embodiments, the first and second regions into which first and second length nanowires 2804 and 2806 are dispersed may be spatially arranged in any manner. For example, in one embodiment, the first region may be an interior region of hemostatic bandage 2800 and the second region may be an exterior region of bandage 2800. For instance, FIG. 31 shows a block diagram cross-sectional view of a hemostatic bandage 3100, which is an example of hemostatic bandage 2800, according to an embodiment. As shown in FIG. 31, hemostatic bandage 3100 includes first length nanowires 2804, a bandage material 3102, and second length nanowires 2806.

Bandage material 3102 contains first length nanowires 2804 in an interior region 3104 of bandage material 3102. Second length nanowires 2806 are contained in a coating 3106 formed over a surface of bandage material 3102.

Hemostatic bandage 3100 increases a rate of blood clotting relative to bandages that do not include a hemostatic element. Longer nanowires, such as second length nanowires 2806, have a higher tissue adhesion ability relative to shorter nanowires, such as first length nanowires 2804, and by being located in coating 3106, enhance tissue adhesion by hemostatic bandage 3100. Furthermore, shorter length nanowires, such as first length nanowires 2804, are more easily incorporated at high concentrations into bandage materials by soaking, filtration, or other procedures, and thus enable a larger total amount of nanowires (and total surface area of nanowires) to be contained by hemostatic bandage 3100 relative to second length nanowires 2806 alone.

Note that steps 2906 and 2908 may be performed separately or simultaneously to form hemostatic bandage 3100. For example, step 2906 may be first performed to disperse first length nanowires 2804 in interior region 3104 of bandage material 3102, and then step 2908 may be formed to form coating 3106 containing second length nanowires 2806 on the surface of bandage material 3102. In a simultaneous dispersing embodiment, referring to FIG. 30, first and second length nanowires 2804 and 2806 may be mixed together by bandage processor 3004, and the mixture may be applied to bandage material 3006. Because first length nanowires 2804 are smaller than second length nanowires 2806, first length nanowires 2804 may penetrate into bandage material 3102 into interior region 3104, while bandage material 3006 (e.g., a fibrous material, etc.) may prevent second length nanowires 2806 from penetrating into bandage material 3102 because of their larger size, and thus second length nanowires 2806 remain at the surface of bandage material 3102.

Figure 32:
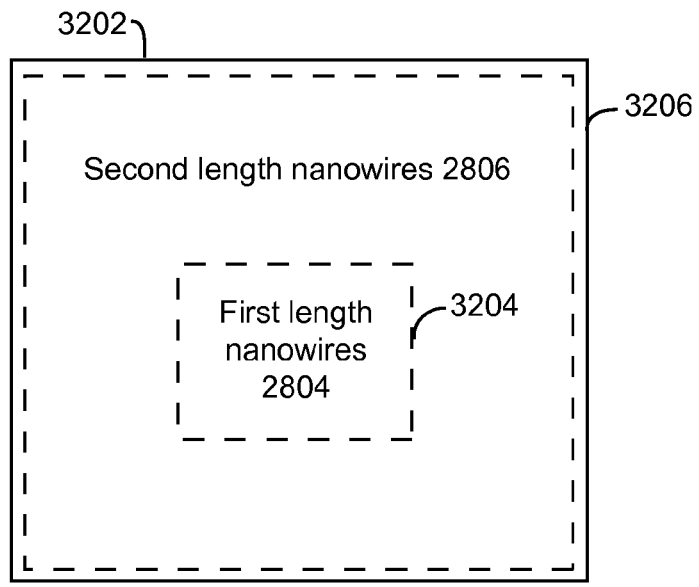
FIG. 32 shows a view of a surface of a hemostatic bandage, according to an embodiment of the present invention.

In another embodiment, the first region may be a central region of a surface of hemostatic bandage 2800 and the second region may be a perimeter region of the surface of bandage 2800. For instance, FIG. 32 shows a view of a surface of a hemostatic bandage 3200, which is an example of hemostatic bandage 2800, according to an embodiment. As shown in FIG. 32, hemostatic bandage 3200 includes first length nanowires 2804, a bandage material 3202, and second length nanowires 2806. Bandage material 3102 contains first length nanowires 2804 in a central region 3204 of the surface of bandage material 3202. Second length nanowires 2806 are contained in a perimeter region 3206 of the surface of bandage material 3202.

Because longer nanowires, such as second length nanowires 2806, have a higher tissue adhesion ability relative to shorter nanowires, perimeter region 3206 may adhere better to a subject than central region 3204, forming a seal with tissue of the subject around central region 3204, which may be positioned adjacent to a wound of the subject.

First and second length nanowires 2804 and 2806, and optionally further lengths of nanowires, may be used in any combination and relative positioning in hemostatic bandages. The different length nanowires may be spatially distributed in the bandage in a controlled manner to impart various degrees of clotting acceleration and tissue adhesion to different portions of the bandage. Furthermore, in embodiments, laminated materials may be used.

Example Hemostatic Surgical Staple and Suture Embodiments

Figure 33:
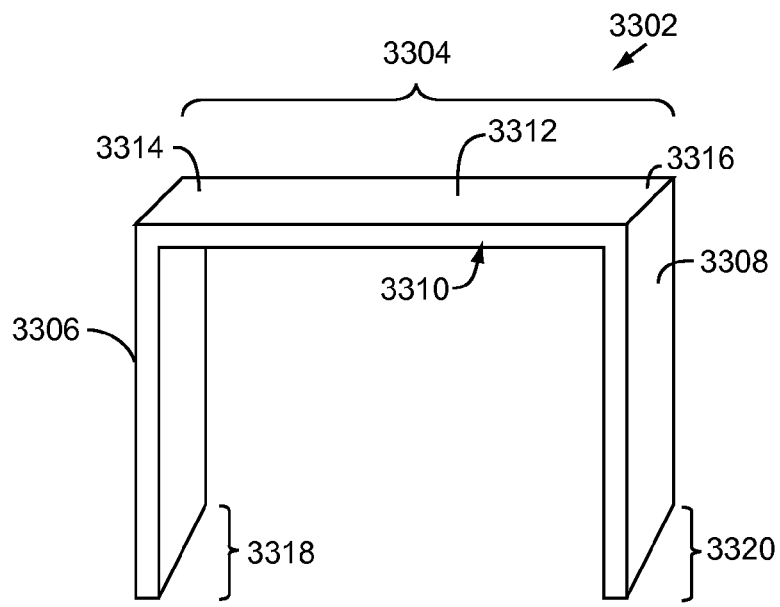
FIG. 33 shows a perspective view of an example surgical staple.

In embodiments, surgical staples and sutures used for suturing wounds may be functionalized with hemostatic nanomaterials to improve clotting. For example, FIG. 33 shows a perspective view of an example surgical staple 3300. As shown in FIG. 33, surgical staple 3300 includes a body 3302 having a base portion 3304, a first leg 3306, and a second leg 3308. Base portion 3304 has opposing first and second surfaces 3310 and 3312. First leg 3306 extends at a first angle (e.g., 90 degrees in FIG. 33) from a first end 3314 of first surface 3310, and second leg 3306 extends at a second angle (e.g., 90 degrees in FIG. 33) from a second end 3316 of first surface 3308. First and second legs 3306 and 3308 each have a respective pointed end portion 3318 and 3320 at a respective end extending away from base portion 3304. Although surgical staple 3300 is shown in FIG. 33 as being a flat piece that is bent, molded, or otherwise formed into a rectangular shape, surgical staple 3300 may have other shapes, including being curved and/or rounded. Surgical staple 3300 may be made from a non resorbable material, such as a metal or a polymer, or may be made from a resorbable material.

When surgical staple 3300 is applied to a subject, pointed end portions 3318 and 3320 of surgical staple 3300 penetrate tissue of the subject, such that legs 3306 and 3308 at least partially penetrate the subject. Legs 3306 and 3308 (and/or base portion 3304) are subsequently bent such that pointed end portions 3318 and 3320 approach each other, overlap each other, are bent past each other, and/or make contact with each other, so that surgical staple 3300 is bonded to the subject, to hold closed a portion of a wound bridged by base portion 3304.

In embodiments, surgical staple 3300 may be functionalized with hemostatic nanostructures to enable faster clotting to occur when staple 3300 is used, relative to non-hemostatic staples. For example, in an embodiment, step 3400 shown in FIG. 34 may be performed. In step 3400, at least a portion of a surgical staple is coated with a layer of nanostructures. Any portion of surgical staple 3300 may be coated with a layer of nanostructures, including surface 3310 (which is in contact with tissue when staple 3300 is in use), legs 3306 and 3308 (which penetrate tissue when staple 3300 is in use), other portion of surgical staple 3300, the entirety of surgical staple 3300, etc.

Figure 34:
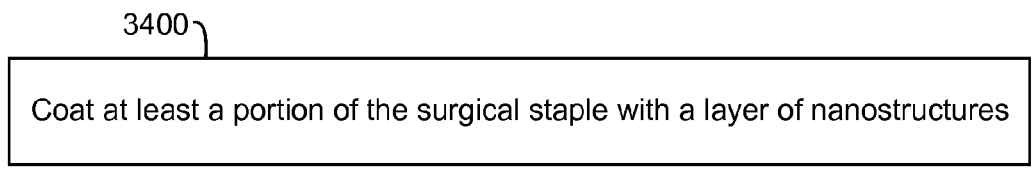
FIG. 34 shows a process for functionalizing a surgical staple with hemostatic nanostructures, according to an example embodiment of the present invention.
Figure 35:
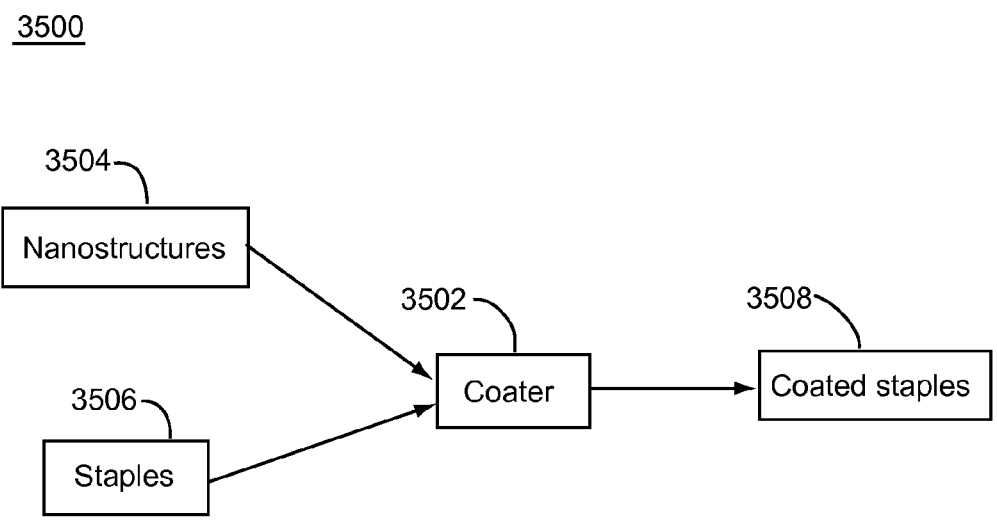
FIG. 35 shows a staple coating system, according to an example embodiment of the present invention.

Step 3400 may be performed in any manner. For instance, FIG. 35 shows a staple coating system 3500, according to an example embodiment of the present invention. Staple coating system 3500 may perform step 3400 in an embodiment. As shown in FIG. 34, system 3500 includes a coater 3502. Coater 3502 receives nanostructures 3504 and staples 3506. Coater 3502 is configured to coat staples 3506 with nanostructures 3504 to generate coated staples 3508. Coater 3502 may be configured to coat a portion or the entirety of each staple of staples 3506, in embodiments. Coater 3502 may coat staples 3506 with nanostructures 3504 in any manner, including by spray coating or soaking staples 3506 in a liquid that includes nanostructures 3504, followed by a drying process, or according to any other suitable technique. In an embodiment, staples 3506 may be imparted with a first charge (either positive or negative), and nanostructures 3504 may be imparted with an opposite second charge, to attract nanostructures 3504 to staples 3506.

In another embodiment, staple coating system 3500 may be configured to perform step 3400 by growing nanostructures directly on staples 3506. Any suitable nanostructure growth technique may be used by staple coating system 3500, including those techniques described elsewhere herein (including those growth techniques disclosed in documents referenced elsewhere herein).

In an embodiment, a shape of surgical staple 3300 may be modified to enable additional nanostructures to coat surgical staple 3300 and to thereby come into contact with the subject.

Figure 36:
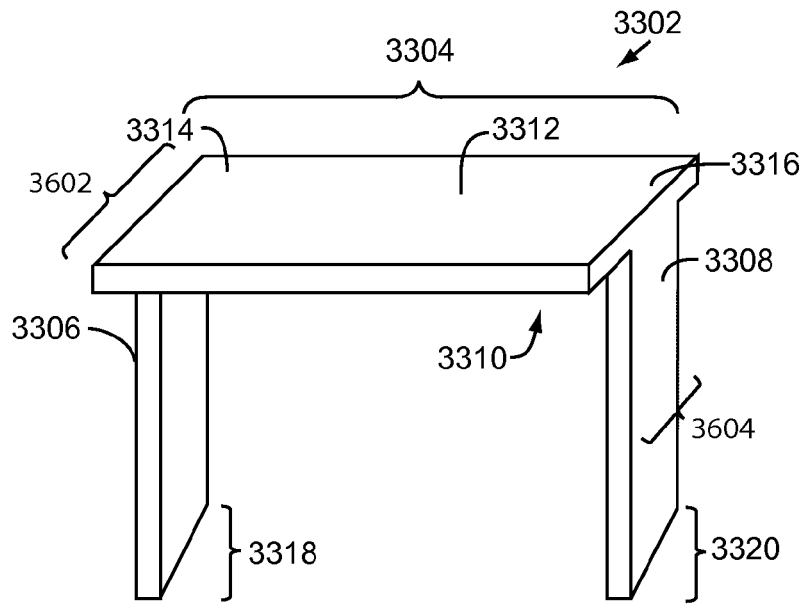
FIG. 36 shows a perspective view of a surgical staple, which is a modified form of the surgical staple of FIG. 33, according to an example embodiment of the present invention.

For example, FIG. 36 shows a perspective view of a surgical staple 3600, which is a modified form of surgical staple 3300, according to an example embodiment of the present invention. Surgical staple 3600 is similar to surgical staple 3300, with differences described as follows. As shown in FIG. 33, base portion 3304 of surgical staple 3300 has a width (perpendicular to an axis along base portion 3304 through first and second ends 3314 and 3316) that is substantially equal to a width of legs 3306 and 3308. As shown in FIG. 36, base portion 3304 of surgical staple 3600 is wider than base portion 3304 of surgical staple 3300. Base portion 3304 of surgical staple 3600 has a first width 3602 (perpendicular to the first axis through first and second ends 3314 and 3316), and first and second legs 3306 and 3308 each have a second width 3604 (parallel to first width 3602) located between base portion 3304 and pointed end portions 3318 and 3320. First width 3602 of base portion 3304 is greater than second width 3604 of first and second legs 3306 and 3308. In this manner, surfaces 3310 and 3312 of base portion 3304 in FIG. 36 have greater surface area than surfaces 3310 and 3312 of base portion 3304 in FIG. 34, and can thus be coated with a greater amount of nanostructures.

Figure 37:
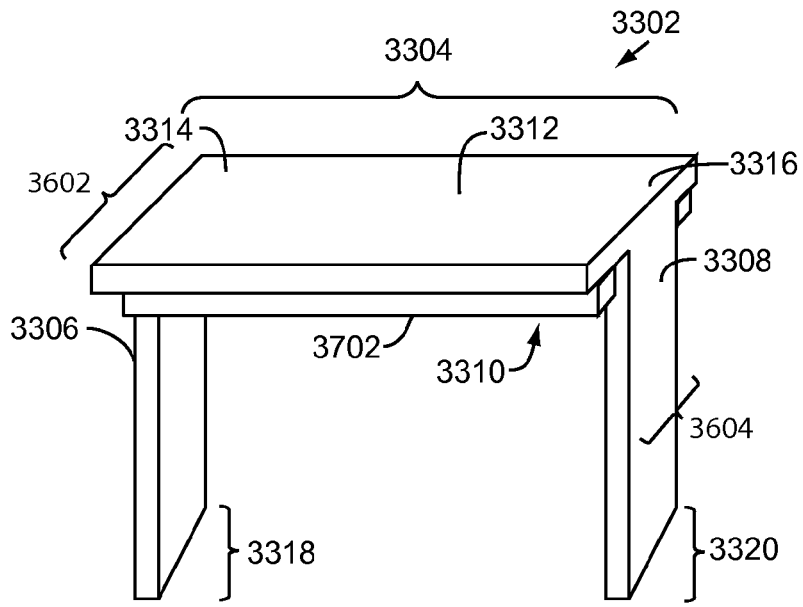
FIG. 37 show a perspective view of the surgical staple of FIG. 36 partially coated with nanostructures, according to an example embodiment of the present invention.

For example, FIG. 37 shows surgical staple 3600 of FIG. 36, where first surface 3310 of base portion 3304 is coated with a layer 3702 of nanostructures. First surface 3310 of base portion 3310 typically comes into contact with tissue of a subject when surgical staple 3600 is applied to the subject. In such case, layer 3702 of nanostructures comes into contact with the tissue, enabling the nanostructures to provide enhanced clotting, as described herein. The nanostructures may be any type of nanostructures described herein, including silicon nanowires, silicon nanofibers, silicon nanoparticles, potassium nanofibers, nanowires/nanofibers/nanoparticles having a thin oxide layer, etc.

Figure 38:
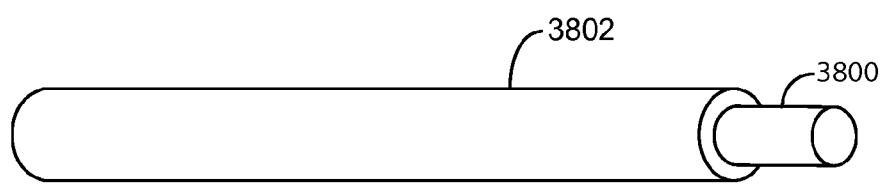
FIG. 38 shows a portion of a suture coated with a layer of nanostructures, according to an example embodiment of the present invention.

In a similar manner as described above, threads/sutures used to hold together wounds in tissue may be functionalized with hemostatic nanomaterials to improve clotting. For example, FIG. 38 shows a portion of a suture 3800 coated with a layer 3802 of nanostructures, according to an example embodiment of the present invention. Suture 3800 may be made of any suitable resorbable materials described elsewhere herein or otherwise known, including natural or synthetic resorbable materials such as polyglycolic acid, polylactic acid, or caprolactone. Suture 3800 may alternatively be made of any suitable non-resorbable materials described elsewhere herein or otherwise known, including artificial fibers such as polypropylene, polyester, nylon, stainless steel, etc. Suture 3800 may be coated with a layer of nanostructures according to a coating system similar to staple coating system 3500 shown in FIG. 35.

Functionalized Nanostructures Embodiments

Figure 39:
FIG. 39 shows an example of a nanofiber functionalized with a material, according to an embodiment of the present invention.

In embodiments, the nanostructures incorporated with structures/materials to form hemostats, as described herein, may be functionalized with additional materials. Such additional materials may improve and/or modify characteristics of the nanostructures. FIG. 39 shows a surface 3902 of a portion of a nanofiber 3900 that is functionalized with a material 3904, according to an embodiment of the present invention.

Nanostructures (such as nanofiber 3900) offer an external surface that can easily be modified using any number of coating or functionalization chemistries (e.g., growth of nitride or carbide layers for improved strength and durability, growth of titanium oxide, Ag, Zn etc. layers for improved biocompatibility with existing implant materials (e.g., titanium), and/or growth of specific organosilanes to facilitate linkage chemistries such as hydrophobic and/or hydrophilic coatings, etc.) developed for attaching biomolecules. For example, a nanofiber surface can be functionalized with a coating material to render it hydrophobic, lipophobic, or amphiphobic. The coating material can comprise, for example, ceramics, polymers, inorganic materials, organic materials, or organic/inorganic hybrid materials including, for example, Teflon®, Tri-sil, tridecafluoro 1,1,2,2, tetrahydrooctyl-l-tricholorosilane, a fluoride containing compound, a silane containing compound, PTFE, hexamethyldisilazane, an aliphatic hydrocarbon containing molecule, an aromatic hydrocarbon containing molecule, a halogen containing molecule and paralyene.

Nanostructures (such as nanofiber 3900) incorporated with structures/materials to form hemostats, as described herein, may be further or alternatively functionalized with one or more hemostatic agents to improve and/or modify their hemostatic characterstics. For example, nanostructures may be functionalized with potassium, fibrin, fibrinogen, thrombin, microfibrillar collagen, polysaccharides, chitosan, zeolite, anhydrous aluminum sulfate, titanium dioxide, antifibrinolytics, and/or further hemostatic agents mentioned elsewhere herein or otherwise known.

Nanostructures in accordance with embodiments of the present invention may be functionalized to target a particular cell, tissue or organ, to enable greater bandage adhesion and/or for further reasons. For instance, techniques and chemistries are known for the precise drug delivery to a particular cell or organ. See, for example, Cotten et al., Methods Enzym. 217:618, 1993, the contents of which are hereby incorporated by reference in its entirety. Nanostructures allow for different functionalization and targeted delivery of different molecules, by "designing" the segments along the length of each nanowire. For example, different segments of the nanowires may be made of different materials, and the different materials may be chosen such that they have different affinities for different functional linking agents or functional moieties.

Examples of materials that may used to functionalize nanostructures, and example techniques for functionalizing nanostructures, are described in U.S. Pub. Appl. No. 2007/0282247, titled "Medical Device Applications of Nanostructured Surfaces," which is incorporated by reference herein in its entirety.

Example Highly-Absorbent Hemostatic Device Embodiments

In embodiments of the present invention, a hemostatic device includes a highly-absorbent scaffold for improved hemostasis. The highly-absorbent scaffold allows large volumes of blood to be absorbed and exposed to hemostatic particles incorporated in the scaffold. Suitable scaffold materials include absorptive polymers, including forms of carboxymethylcellulose (CMC) and alginates, or combinations thereof. Suitable hemostatic particles include inorganic particles such as silicon particles and silicon dioxide particles, or combinations thereof. Without being bound to a particular theory of operation, it is believed that the improved absorption of the scaffold causes improved interaction between blood and hemostasis-inducing particles, thereby resulting in faster and more efficient initiation of the contact coagulation pathway.

In one embodiment, the scaffold comprises a highly-absorbent swelling material. In another embodiment, the scaffold includes a gelling agent or gel-forming material. In a preferred embodiment, a hemostatic scaffold for incorporation into a hemostatic device includes one or more materials which swell and form a gel upon contact with blood, thereby allowing large volumes of blood to be exposed to hemostatic particles incorporated within the scaffold material. The improved absorbance of the scaffold allows for more physical interaction between the absorbed blood and inorganic surfaces upon which the contact coagulation pathway is initiated. This allows for better and faster hemostasis due to the improved absorbance of blood and the respective increased interaction between blood and hemostatic particles.

Embodiments of the invention include a scaffold comprising one or more gelling agents capable of absorbing significant amounts of fluid. Examples of such materials include gelling polymers or other hydrocolloid-based materials. In preferred embodiments, the scaffold comprises any fibrous material capable of absorbing greater than about ten times its own weight in fluid. Most preferably, the scaffold comprises forms of carboxymethylcellulose (CMC) and/or alginates. The composition of the absorbent scaffold can be modified to suit the needs of a specific application, as will be appreciated by persons of ordinary skill in the art. For example, CMC can be formulated in a variety of ways, and the form of CMC used can depend on the type or structure of the scaffold. For example, a highly absorbent pad can be produced using CMC, and such a pad can be loaded with inorganic, hemostatic particles such that the pad will induce hemostasis at a bleeding site.

The scaffold can be formed by any available methods known in the art, including those mentioned herein. For example, the scaffold can comprise woven fibers. In alternative embodiments, the scaffold may be a solid material, fiber bundles, a plurality of layers of a solid material rather than a weave of fibers, or any other available woven or nonwoven structure available in the relevant art or mentioned elsewhere herein. As will be appreciated by those of skill in the relevant art, the scaffold can be incorporated into a variety of hemostatic devices, as described herein (e.g. hemostatic bandages, pads, or plugs).

The present invention further involves the incorporation of hemostatic particles (e.g., inorganic hemostatic particles) onto a highly absorbent scaffold that absorbs fluids and gels upon contact with blood such that the combined inorganic particle/absorbent matrix becomes more hemostatic than the absorbent matrix alone. Appropriate materials for the particles integrated into the scaffold can include any hemostatic particles known in the art or described herein. In a preferred embodiment, the matrix comprises CMC fibers and the inorganic particles that activate the contact coagulation pathway include inorganic fibers. The hemostatic particles can include any hemostatic particles known in the art, including clays and metal oxides. Preferably, the hemostatic particles include silicon or silicon dioxide (e.g., silicon nanofibers, silicon dioxide nanofibers, or fumed silica). In certain embodiments, the hemostatic particles include a combination of fibers of different materials and/or sizes. In yet another embodiment, the individual fibers comprise a combination of materials.

The hemostatic particles can comprise nanowires, nanofibers, nanorods, or other nanostructures described herein. The particles can optionally include heterostructures, e.g., core-shell structures or axially-varied nanostructures, as described herein.

The inorganic fibers can include hemostatic particles (e.g., silicon or silicon dioxide particles) ranging from about 5 nm to about 100 nm in diameter and about 1 micron to about 1000 microns in length. Alternatively, particles with one dimension between about 1 nm and about 100 microns in size could be used. Alternatively, silicon dioxide particles with one dimension between about 1 nm and about 100 microns in size could be used. Alternatively, any inorganic particles that could activate the contact coagulation pathway with one dimension between 1 nm and 100 microns in size could be used. As will be appreciated by persons of ordinary skill in the art, the size and/or composition of the hemostatic particles can be varied to meet the needs of a particular application. For example, as described herein, shorter nanowires can penetrate more deeply and provide extra surface area for enhanced clotting, while longer nanowires tend to remain at the bandage surface and provide better tissue adhesion. Thus, the size-related features of the nanowires can be used to provide an appropriate arrangement of hemostatic particles in/on the scaffold.

Integration of hemostatic or other particles and the scaffold structure (i.e., incorporating the particles in/on the scaffold) can include any available methods known in the art, including any of the coating methods described herein. For example, integration can be effectuated by any chemical or mechanical bond or force, including linking agents, covalent attachment, Van der Waals attraction, adsorption, and charge-based attraction. Methods of integration can include any available methods known in the art or mentioned herein, including nano-spinning, weaving, pouring, injecting, flowing, mixing, spraying, dip coating, and soaking Preferred methods for coating the scaffold include suspending the inorganic particles in a solvent that would not dissolve the polymeric fibers or cause them to turn into a gel. The polymeric scaffold could then be saturated in the solution containing the inorganic particles (e.g., by dip coating) and the solvent driven off to leave the particles attached to the polymeric fibers. As will be appreciated by persons of ordinary skill in the art, the method for incorporation of the hemostatic particles into the scaffold can be varied depending on the scaffold material, the hemostatic particles, and the needs of the particular application.

The arrangement or pattern of particles and the density at which particles are applied to the scaffold can be varied throughout the scaffold to achieve optimum hemostasis, conformation to a subject, or other results. For example, the particles can be applied to the scaffold fibers in a uniform manner. Alternatively, the particles can be selectively applied to portions of the scaffold according to any arrangements described herein or known in the art. For example, the particle features (e.g., size, shape, structure, or material) can vary throughout the scaffold material to achieve certain effects including optimized hemostasis or appropriate levels of hemostasis depending on the application. Any appropriate method of arrangement can be used, including those known in the art or described herein. For example, an appropriate arrangement and mixture of different lengths of nanowires may be spatially distributed in the scaffold in a controlled manner to impart various degrees of clotting acceleration and tissue adhesion to different portions of the scaffold.

Additionally, the density at which particles are applied to the scaffold can be varied to achieve optimum hemostasis, controlled hemostasis, conformation to a subject, or other tailored results. FIGS. 43A-43D show CMC scaffolds loaded with silicon nanofibers at densities appropriate for platelet binding and hemostasis, according to embodiments of the present invention. Preferably, the density of the inorganic particles should be controlled such that maximal hemostatic activity is achieved without deleteriously affecting the advantageous properties of the scaffold (e.g. flexibility, absorptivity). Preferably, the inorganic particles are dispersed throughout the scaffold material(s) such that the particles are entrapped by the scaffold but do not tightly coat the polymer, thereby creating an additional surface at which accelerated hemostasis can occur. Preferably, the hemostatic particles and the scaffold material(s) are integrated in a manner (e.g., in a particular ratio) such that nanostructures are entrapped by the scaffold but do not tightly coat the scaffold. In this manner, an additional surface at which accelerated hemostasis can occur is provided by the hemostatic particles without blocking the surface of the scaffold. The density of particles can be modified prior to integration with a barrier material or scaffold. In certain embodiments, the density of inorganic fibers in the scaffold can be any density between about 0 mg/cm$^2$ and about 100 mg/cm$^2$. In a preferred embodiment, the density of inorganic fibers in the scaffold is between about 0.05 mg/cm$^2$ and about 2 mg/cm$^2$, for example about 0.5 mg/cm$^2$.

In certain embodiments of the invention, the hemostatic particles can be modified or functionalized in any manner known in the art or described herein. For example, inorganic nanofibers can be functionalized with a coating material to render them hydrophobic, lipophobic, or amphiphobic. Nanostructures may be further or alternatively functionalized with one or more hemostatic agents to improve and/or modify their hemostatic characterstics. For example, nanostructures may be functionalized with potassium, fibrin, fibrinogen, thrombin, microfibrillar collagen, polysaccharides, chitosan, zeolite, anhydrous aluminum sulfate, titanium dioxide, antifibrinolytics, and/or further hemostatic agents mentioned elsewhere herein or otherwise known. In certain embodiments, the integrated particles can be functionalized to target a particular cell, tissue, or organ to achieve specific binding with a particular cell, tissue, or organ or to enable greater bandage adhesion, etc. As described herein, different segments of nanostructures may be made of different materials, and the different materials may be chosen such that they have different affinities for different functional linking agents or functional moieties.

Figure 44:
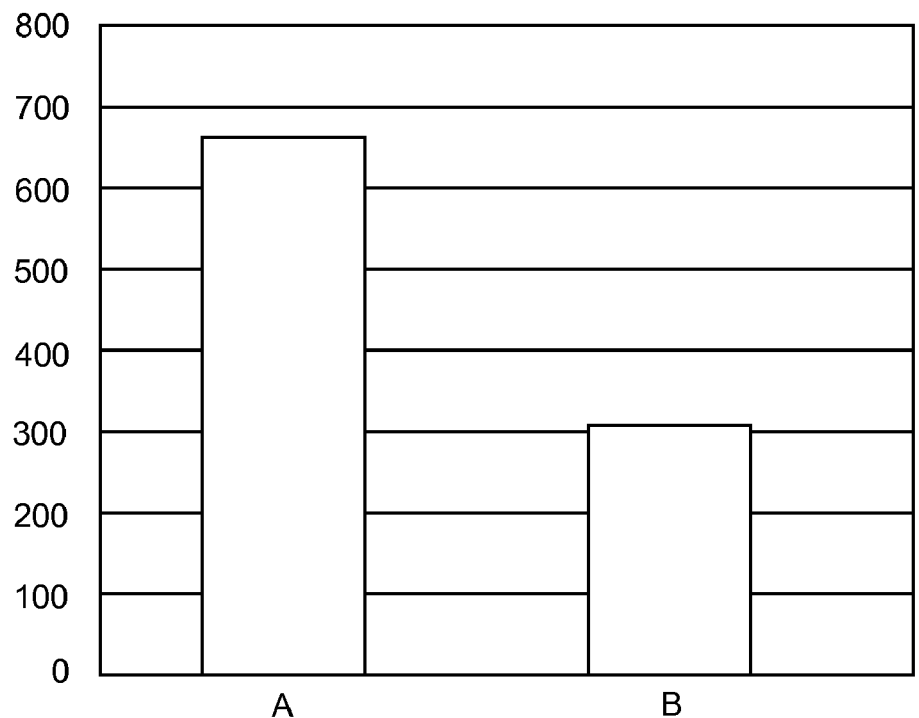
FIGS. 44 and 45 show graphs illustrating the hemostatic efficacy of CMC fibers coated with silicon nanofibers compared to uncoated CMC fibers, according to embodiments of the present invention.
Figure 45:
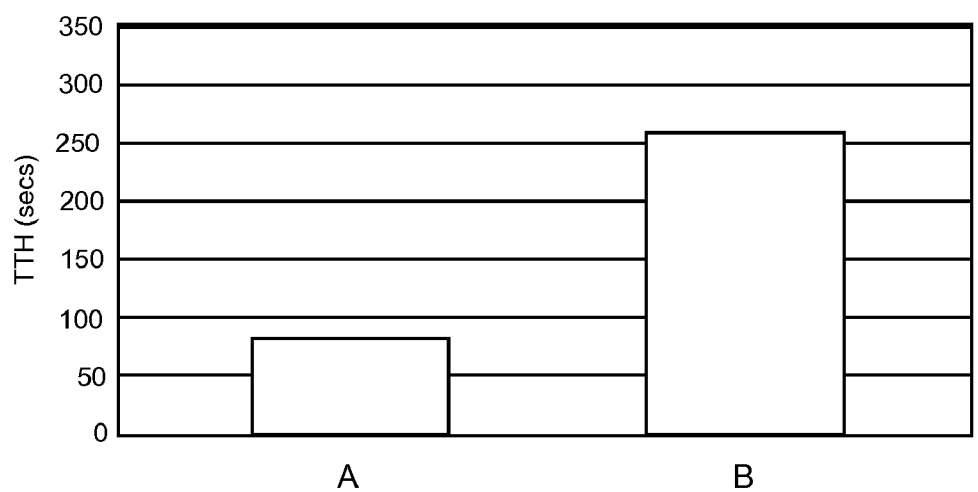

FIGS. 44 and 45 show graphs illustrating the hemostatic efficacy of CMC fibers coated with silicon nanofibers, according to embodiments of the present invention, compared to uncoated CMC fibers. FIG. 44 reveals in vitro data showing that blood that has been in contact with a 2 cm$^2$ piece of CMC scaffold coated with about 0.5 mg/cm$^2$ silicon nanofibers (sample B) has the clot formation time (vertical axis) reduced by more than 50% compared with an uncoated CMC scaffold (sample A), as measured by a thromboelastograph (TEG). These results indicate that the nanofiber coating improves hemostasis for the CMC scaffold.

FIG. 45 shows test results of an uncoated CMC scaffold (sample B) and a CMC scaffold coated with 0.5 mg/cm$^2$ silicon nanofibers (sample A), according to embodiments of the present invention. Coated and uncoated scaffolds were tested to determine their hemostatic efficacy in a swine liver injury model. A 5 mm biopsy punch was used to create the liver wound and then the punched center was excised. A 2 cm$^2$ piece of coated or uncoated CMC scaffold was placed over the wound and light pressure was applied using gauze placed over the CMC test sample. Every 30 seconds the gauze was removed and the test sample observed for bleeding (blood escaping around or through the test sample). If no blood loss was seen after 30 seconds of observation the time to hemostasis was recorded. The CMC scaffold coated with silicon nanofibers showed a much faster time to hemostasis (TTH, vertical axis) compared to the uncoated CMC scaffold.

Example Platelet Binding Device Embodiments

In additional aspects of the invention, platelet binding methods and devices are provided. In an example embodiment, nanostructures are provided which induce platelet binding (e.g., silicon nanofibers or silicon dioxide nanofibers). As described above in reference to other device embodiments of the present invention, example embodiments include nanostructures integrated with a base structure. The base structure is assembled to receive platelets and promote platelet adherence at the nanostructure surfaces integrated with the base structure. The platelet binding device can include any of the above-mentioned embodiments of the invention, including a hemostatic device, a wound-healing device such as a wound dressing, a specific cell binding device; a cell, tissue, or organ targeting device; a platelet collection device, a platelet filtration device, a platelet analysis device, or other devices. As will be appreciated by those of skill in the relevant art(s), platelet binding devices can be suitably formed for any application where platelet binding is desirable. For example, a silicon nanofiber-coated base structure could be used to promote specific binding between the nanofibers and platelets, and the device could be used for medical device or other applications.

Conclusion

Exemplary embodiments of the present invention have been presented. The invention is not limited to these examples. These examples are presented herein for purposes of illustration, and not limitation. Alternatives (including equivalents, extensions, variations, deviations, etc., of those described herein) will be apparent to persons skilled in the relevant art(s) based on the teachings contained herein. Such alternatives fall within the scope and spirit of the invention.

All publications, patents and patent applications mentioned in this specification are herein incorporated by reference to the same extent as if each individual publication, patent or patent application was specifically and individually indicated to be incorporated by reference.

What is claimed is:

1. A platelet binding structure, comprising:
   a base structure that comprises carboxymethylcellulose (CMC); and
   a plurality of inorganic nanostructures incorporated with the base structure wherein the nanostructures are incorporated in the base structure at a density of between about 0.05 mg/cm$^2$ and about 100 mg/cm$^2$;
   wherein the nanostructures are configured to induce platelet binding when the platelet binding structure is contacted with platelets.

2. The platelet binding structure of claim 1, wherein the platelet binding structure is a hemostatic device, a wound dressing, a specific cell binding device, or a platelet filtration device.

3. The platelet binding structure of claim 1, wherein the nanostructures comprise elongated nanofibers.

4. The platelet binding structure of claim 3, wherein the nanostructures comprise silicon nanofibers and/or silicon dioxide nanofibers.

5. The platelet binding structure of claim 1, wherein the nanostructures coat the base structure.

6. The platelet binding structure of claim 1 wherein the nanostructures are incorporated in the base structure at a density of between about 0.05 and 2 mg/cm$^2$.

7. The platelet binding structure of claim 1 wherein the nanostructures are incorporated in the base structure at a density of between about 0.05 and 0.5 mg/cm$^2$.

8. The platelet binding structure of claim 1 wherein at least about three times more platelets bind to the nanofiber coated CMC base structure as compared with an uncoated CMC base structure.

9. A method of inducing platelet adhesion, comprising:
   contacting a plurality of inorganic nanostructures incorporated within a base structure comprising carboxymethylcellulose (CMC) with a population of platelets, wherein the nanostructures are incorporated in the base structure at a density of between about 0.05 mg/cm$^2$ and about 100 mg/cm$^2$.

10. The method of claim 9, further comprising suspending the inorganic nanostructures in a solvent and coating the base structure with the solvent prior to said contacting.

11. The method of claim 10, wherein said coating comprises dip coating.

12. The method of claim 9, wherein the nanostructures comprise elongated nanofibers.

13. The method of claim 12, wherein the nanostructures comprise silicon nanofibers and/or silicon dioxide nanofibers.

14. The method of claim 9, wherein the nanostructures are incorporated in the base structure at a density of between about 0.05 mg/cm$^2$ and about 2 mg/cm$^2$.

15. The method of claim 9, wherein the nanostructures are incorporated in the base structure at a density of between about 0.05 and 0.5 mg/cm$^2$.

16. The method of claim 9, wherein at least about three times more platelets bind to the nanofiber coated CMC base structure as compared with an uncoated CMC base structure.

17. A hemostatic structure, comprising:
a base structure that includes a first material capable of creating a gel when contacted with blood; and
a plurality of hemostatic inorganic nanoparticles incorporated with the base structure wherein the hemostatic nanoparticles have a density in the range of about 0.05 mg per square centimeter of the base structure and about 2 mg per square centimeter of the base structure;
wherein the hemostatic nanoparticles are configured to induce hemostasis when the hemostatic structure is contacted with blood.

18. The hemostatic structure of claim 17, wherein the first material comprises carboxymethylcellulose.

19. The hemostatic structure of claim 17, wherein the first material comprises alginic acid.

20. The hemostatic structure of claim 17, wherein the first material is capable of absorbing at least 10 times its own weight in fluid.

21. The hemostatic structure of claim 17, wherein the hemostatic nanoparticles comprise elongated nanofibers.

22. The hemostatic structure of claim 21, wherein the hemostatic nanoparticles comprise silicon nanofibers and/or silicon dioxide nanofibers.

23. The hemostatic structure of claim 17, wherein the hemostatic nanoparticles coat the base structure.

24. The hemostatic structure of claim 17, wherein the base structure is porous.

25. A method for forming a hemostatic structure, comprising:
providing a base structure that includes a first material capable of creating a gel when contacted with blood; and
coating the base structure with a plurality of hemostatic inorganic nanoparticles comprising elongated silicon nanofibers and/or silicon dioxide nanofibers such that the nanoparticles are configured to induce hemostasis when the hemostatic structure is contacted with blood, wherein said coating comprises suspending the inorganic nanofibers in a solvent and coating the base structure with the solvent.

26. The method of claim 25, wherein the base structure comprises carboxymethylcellulose.

27. The method of claim 25, wherein said coating comprises dip coating.

28. The method of claim 27, further comprising evaporating the solvent after said coating to leave a plurality of nanofibers attached to the base structure.

29. The method of claim 28, wherein the nanofibers attach to the base structure substantially by Van der Waals attraction.

* * * * *